(12) United States Patent
Hahn et al.

(10) Patent No.: US 11,490,811 B2
(45) Date of Patent: Nov. 8, 2022

(54) WAFERSCALE PHYSIOLOGICAL CHARACTERISTIC SENSOR PACKAGE WITH INTEGRATED WIRELESS TRANSMITTER

(71) Applicant: Medtronic MiniMed, Inc., Northridge, CA (US)

(72) Inventors: Daniel Hahn, Tustin, CA (US); David L. Probst, Chandler, AZ (US); Randal C. Schulhauser, Phoenix, AZ (US); Mohsen Askarinya, Chandler, AZ (US); Patrick W. Kinzie, Glendale, AZ (US); Thomas P. Miltich, Otsego, MN (US); Mark D. Breyen, Champlin, MN (US); Santhisagar Vaddiraju, Plymouth, MN (US)

(73) Assignee: Medtronic MiniMed, Inc., Northridge, CA (US)

( * ) Notice: Subject to any disclaimer, the term of this patent is extended or adjusted under 35 U.S.C. 154(b) by 153 days.

(21) Appl. No.: 17/112,394

(22) Filed: Dec. 4, 2020

(65) Prior Publication Data
US 2021/0106226 A1    Apr. 15, 2021

Related U.S. Application Data

(63) Continuation of application No. 15/716,424, filed on Sep. 26, 2017, now Pat. No. 10,874,300.

(51) Int. Cl.
*A61B 5/00*      (2006.01)
*H01L 21/48*     (2006.01)
(Continued)

(52) U.S. Cl.
CPC .......... *A61B 5/0004* (2013.01); *A61B 5/1468* (2013.01); *A61B 5/14532* (2013.01);
(Continued)

(58) Field of Classification Search
CPC . A61B 5/0004; A61B 5/14532; A61B 5/1468; A61B 5/1486; A61B 5/14865;
(Continued)

(56) References Cited

U.S. PATENT DOCUMENTS 4,755,173 A    7/1988  Konopka et al.
5,391,250 A    2/1995  Cheney, II et al.
(Continued)

OTHER PUBLICATIONS

Prosecution History from U.S. Appl. No. 15/716,424, dated Jul. 17, 2019 through Nov. 6, 2020, 82 pp.
(Continued)

*Primary Examiner* — Shahed Ahmed
*Assistant Examiner* — Vicki B. Booker
(74) *Attorney, Agent, or Firm* — Shumaker & Sieffert, P.A.

(57) ABSTRACT

An embodiment of a sensor device includes a base substrate, a circuit pattern formed overlying the interior surface of the substrate, a physiological characteristic sensor element on the exterior surface of the substrate, conductive plug elements located in vias formed through the substrate, each conductive plug element having one end coupled to a sensor electrode, and having another end coupled to the circuit pattern, a multilayer component stack carried on the substrate and connected to the circuit pattern, the stack including features and components to provide processing and wireless communication functionality for sensor data obtained in association with operation of the sensor device, and an enclosure structure coupled to the substrate to enclose the interior surface of the substrate, the circuit pattern, and the stack.

20 Claims, 17 Drawing Sheets

(51) Int. Cl.
  *H01L 21/52* (2006.01)
  *H01L 21/78* (2006.01)
  *H01L 23/055* (2006.01)
  *H01L 23/498* (2006.01)
  *H01L 23/66* (2006.01)
  *A61B 5/145* (2006.01)
  *A61B 5/1468* (2006.01)
  *A61B 5/1486* (2006.01)
  *H01L 23/31* (2006.01)

(52) U.S. Cl.
  CPC ........ *H01L 21/486* (2013.01); *H01L 21/4817* (2013.01); *H01L 21/4853* (2013.01); *H01L 21/52* (2013.01); *H01L 21/78* (2013.01); *H01L 23/055* (2013.01); *H01L 23/4985* (2013.01); *H01L 23/49827* (2013.01); *H01L 23/49838* (2013.01); *H01L 23/66* (2013.01); *A61B 5/1486* (2013.01); *A61B 5/14865* (2013.01); *A61B 2562/12* (2013.01); *H01L 23/3121* (2013.01); *H01L 2223/6677* (2013.01)

(58) Field of Classification Search
  CPC ............ A61B 2562/12; H01L 21/4817; H01L 21/4853; H01L 21/486; H01L 21/52; H01L 21/78; H01L 23/055; H01L 23/49827; H01L 23/49838; H01L 23/4985; H01L 23/66; H01L 23/3121; H01L 2223/6677; H01L 2224/131; H01L 2224/16145; H01L 2224/16227; H01L 2224/17181; H01L 2224/32145; H01L 2224/32225; H01L 2225/06513; H01L 2225/06517
  See application file for complete search history.

(56) References Cited

U.S. PATENT DOCUMENTS

| | | | |
|---|---|---|---|
| 5,485,408 A | 1/1996 | Blomquist | |
| 5,522,803 A | 6/1996 | Teissen-Simony | |
| 5,665,065 A | 9/1997 | Colman et al. | |
| 5,800,420 A | 9/1998 | Gross et al. | |
| 5,807,375 A | 9/1998 | Gross et al. | |
| 5,925,021 A | 7/1999 | Castellano et al. | |
| 5,954,643 A | 9/1999 | Van Antwerp et al. | |
| 6,017,328 A | 1/2000 | Fischell et al. | |
| 6,186,982 B1 | 2/2001 | Gross et al. | |
| 6,246,992 B1 | 6/2001 | Brown | |
| 6,248,067 B1 | 6/2001 | Causey, III et al. | |
| 6,248,093 B1 | 6/2001 | Moberg | |
| 6,355,021 B1 | 3/2002 | Nielsen et al. | |
| 6,379,301 B1 | 4/2002 | Worthington et al. | |
| 6,544,212 B2 | 4/2003 | Galley et al. | |
| 6,558,351 B1 | 5/2003 | Steil et al. | |
| 6,591,876 B2 | 7/2003 | Safabash | |
| 6,641,533 B2 | 11/2003 | Causey, III et al. | |
| 6,736,797 B1 | 5/2004 | Larsen et al. | |
| 6,749,587 B2 | 6/2004 | Flaherty | |
| 6,766,183 B2 | 7/2004 | Walsh et al. | |
| 6,801,420 B2 | 10/2004 | Talbot et al. | |
| 6,804,544 B2 | 10/2004 | Van Antwerp et al. | |
| 6,892,085 B2 | 5/2005 | Melvor et al. | |
| 7,003,336 B2 | 2/2006 | Holker et al. | |
| 7,029,444 B2 | 4/2006 | Shin et al. | |
| 7,066,909 B1 | 6/2006 | Peter et al. | |
| 7,137,964 B2 | 11/2006 | Flaherty | |
| 7,303,549 B2 | 12/2007 | Flaherty et al. | |
| 7,399,277 B2 | 7/2008 | Saidara et al. | |
| 7,442,186 B2 | 10/2008 | Blomquist | |
| 7,468,033 B2 | 12/2008 | Van Antwerp et al. | |
| 7,602,310 B2 | 10/2009 | Mann et al. | |
| 7,647,237 B2 | 1/2010 | Malave et al. | |
| 7,699,807 B2 | 4/2010 | Faust et al. | |
| 7,727,148 B2 | 6/2010 | Talbot et al. | |
| 7,785,313 B2 | 8/2010 | Mastrototaro | |
| 7,806,886 B2 | 10/2010 | Kanderian, Jr. et al. | |
| 7,819,843 B2 | 10/2010 | Mann et al. | |
| 7,828,764 B2 | 11/2010 | Moberg et al. | |
| 7,879,010 B2 | 2/2011 | Hunn et al. | |
| 7,890,295 B2 | 2/2011 | Shin et al. | |
| 7,892,206 B2 | 2/2011 | Moberg et al. | |
| 7,892,748 B2 | 2/2011 | Norrild et al. | |
| 7,901,394 B2 | 3/2011 | Ireland et al. | |
| 7,942,844 B2 | 5/2011 | Moberg et al. | |
| 7,946,985 B2 | 5/2011 | Mastrototaro et al. | |
| 7,955,305 B2 | 6/2011 | Moberg et al. | |
| 7,963,954 B2 | 6/2011 | Kavazov | |
| 7,977,112 B2 | 7/2011 | Burke et al. | |
| 7,979,259 B2 | 7/2011 | Brown | |
| 7,985,330 B2 | 7/2011 | Wang et al. | |
| 8,024,201 B2 | 9/2011 | Brown | |
| 8,100,852 B2 | 1/2012 | Moberg et al. | |
| 8,114,268 B2 | 2/2012 | Wang et al. | |
| 8,114,269 B2 | 2/2012 | Cooper et al. | |
| 8,137,314 B2 | 3/2012 | Mounce et al. | |
| 8,181,849 B2 | 5/2012 | Bazargan et al. | |
| 8,182,462 B2 | 5/2012 | Istoc et al. | |
| 8,192,395 B2 | 6/2012 | Estes et al. | |
| 8,195,265 B2 | 6/2012 | Goode, Jr. et al. | |
| 8,202,250 B2 | 6/2012 | Stutz, Jr. | |
| 8,207,859 B2 | 6/2012 | Enegren et al. | |
| 8,226,615 B2 | 7/2012 | Bikovsky | |
| 8,257,259 B2 | 9/2012 | Brauker et al. | |
| 8,267,921 B2 | 9/2012 | Yodfat et al. | |
| 8,275,437 B2 | 9/2012 | Brauker et al. | |
| 8,277,415 B2 | 10/2012 | Mounce et al. | |
| 8,292,849 B2 | 10/2012 | Bobroff et al. | |
| 8,298,172 B2 | 10/2012 | Nielsen et al. | |
| 8,303,572 B2 | 11/2012 | Mair et al. | |
| 8,305,580 B2 | 11/2012 | Aasmul | |
| 8,308,679 B2 | 11/2012 | Hanson et al. | |
| 8,313,433 B2 | 11/2012 | Cohen et al. | |
| 8,318,443 B2 | 11/2012 | Norrild et al. | |
| 8,323,250 B2 | 12/2012 | Chong et al. | |
| 8,343,092 B2 | 1/2013 | Rush et al. | |
| 8,352,011 B2 | 1/2013 | Van Antwerp et al. | |
| 8,353,829 B2 | 1/2013 | Say et al. | |
| 9,295,786 B2 | 3/2016 | Gottlieb et al. | |
| 2002/0022855 A1 | 2/2002 | Bobroff et al. | |
| 2007/0123819 A1 | 5/2007 | Mernoe et al. | |
| 2008/0255440 A1 | 10/2008 | Eilersen et al. | |
| 2010/0160861 A1 | 6/2010 | Causey, III et al. | |
| 2011/0057327 A1 | 3/2011 | Yoshida et al. | |
| 2011/0077490 A1 | 3/2011 | Simpson et al. | |
| 2011/0272786 A1 | 11/2011 | Besling et al. | |
| 2012/0101540 A1 | 4/2012 | O'Brien et al. | |
| 2016/0058353 A1 | 3/2016 | Vaides et al. | |
| 2016/0235346 A1 | 8/2016 | Liu et al. | |
| 2017/0020415 A1 | 1/2017 | Scherer et al. | |
| 2017/0020458 A1 | 1/2017 | Yee et al. | |
| 2017/0227533 A1 | 8/2017 | Lin et al. | |
| 2017/0238856 A1 | 8/2017 | Botvinick et al. | |
| 2018/0235544 A1* | 8/2018 | Nagarkar ................ C23C 14/34 |
| 2019/0090742 A1 | 3/2019 | Hahn et al. | |
| 2019/0090743 A1 | 3/2019 | Hahn et al. | |

OTHER PUBLICATIONS

Prosecution History from U.S. Appl. No. 15/716,426, dated Oct. 4, 2018 through Feb. 6, 2020, 48 pp.

\* cited by examiner

WAFERSCALE PHYSIOLOGICAL CHARACTERISTIC SENSOR PACKAGE WITH INTEGRATED WIRELESS TRANSMITTER

This application is a continuation of U.S. patent application Ser. No. 15/716,424, (issued as U.S. Pat. No. 10,874,300), entitled "WAFERSCALE PHYSIOLOGICAL CHARACTERISTIC SENSOR PACKAGE WITH INTEGRATED WIRELESS TRANSMITTER," and filed on Sep. 26, 2017, the entire content of which is incorporated herein by reference.

TECHNICAL FIELD

Embodiments of the subject matter described herein relate generally to medical devices. More particularly, embodiments of the subject matter relate to physiological sensor devices and related manufacturing processes.

BACKGROUND

The prior art includes a wide variety of medical devices and components, related manufacturing techniques, and related packaging techniques. For example, physiological characteristic sensors are generally known in the art for use in a variety of specialized applications. In this regard, thin film electrochemical sensors are used to test analyte levels in patients. More specifically, thin film sensors have been designed for use in obtaining continuous and real-time blood glucose (BG) levels and monitoring BG levels in a diabetic patient, with the distal segment portion of the sensor positioned subcutaneously in direct contact with patient extracellular fluid. Such readings can be especially useful in adjusting a treatment regimen which typically includes regular administration of insulin to the patient.

A glucose sensor of the type described above may be packaged and sold as a product that includes certain features or components that allow the patient to position and subcutaneously implant the sensor. For example, thin film glucose sensors are often implanted subcutaneously/transcutaneously using an introducer tool, which may be packaged with the glucose sensor. The introducer contains a needle that is used to puncture the skin of a patient at the same time as the sensor is introduced. The needle is then withdrawn, leaving the sensor in the skin of the patient. The introducer, or insertion device, commonly including a needle, is used and then discarded after inserting the sensor at the sensor site.

A continuous glucose sensor of the type described above can include electrical and physical features that allow the sensor to be electrically and physically connected to a wireless transmitter unit. In accordance with a typical use case, the transmitter unit is connected to the glucose sensor after the sensor is deployed and affixed to the skin of the patient. Conventional transmitter units are durable components that are designed to be "reused" with multiple glucose sensors, which are disposable components having a relatively short lifespan, e.g., several days. Handling, managing, and deploying such continuous glucose sensors and their compatible wireless transmitter units can be frustrating, difficult, and time consuming from the patient perspective.

Accordingly, it is desirable to have a cost efficient solution that integrates a physiological characteristic sensor and a wireless transmitter into a single device package. In addition, it is desirable to have a cost efficient and effective fabrication methodology to manufacture an integrated sensor device package. Furthermore, other desirable features and characteristics will become apparent from the subsequent detailed description and the appended claims, taken in conjunction with the accompanying drawings and the foregoing technical field and background.

BRIEF SUMMARY

Various embodiments of a physiological characteristic sensor device (e.g., a continuous glucose sensor) and related manufacturing processes are disclosed here.

In accordance with an embodiment, a physiological characteristic sensor device includes: a base substrate having an exterior surface and an interior surface opposing the exterior surface; a conductive circuit pattern formed overlying the interior surface of the base substrate; a physiological characteristic sensor element located on the exterior surface of the base substrate, the physiological characteristic sensor element comprising sensor electrodes; conductive plug elements located in vias formed through the base substrate, each conductive plug element having a first end electrically coupled to one of the sensor electrodes, and having a second end electrically coupled to the conductive circuit pattern; a multilayer component stack carried on the base substrate and connected to the conductive circuit pattern, the multilayer component stack including features and components to provide processing and wireless communication functionality for sensor data obtained in association with operation of the physiological characteristic sensor device; and an enclosure structure coupled to the base substrate to enclose the interior surface of the base substrate, the conductive circuit pattern, and the multilayer component stack.

In accordance with an embodiment, a physiological characteristic sensor device includes: a base substrate having an exterior surface and an interior surface opposing the exterior surface; a conductive circuit pattern formed overlying the interior surface of the base substrate; a glucose sensor element located on the exterior surface of the base substrate, the glucose sensor element comprising sensor electrodes; conductive plug elements located in vias formed through the base substrate, each conductive plug element having a first end electrically coupled to one of the sensor electrodes, and having a second end electrically coupled to the conductive circuit pattern; a multilayer component stack carried on the base substrate and connected to the conductive circuit pattern, the multilayer component stack including features and components to provide processing and wireless communication functionality for sensor data obtained in association with operation of the glucose sensor element, and the multilayer component stack including an active layer, a passive component layer, and a power source component layer; and an enclosure structure coupled to the base substrate to enclose the interior surface of the base substrate, the conductive circuit pattern, and the multilayer component stack.

In accordance with an embodiment, a physiological characteristic sensor device includes: an enclosure structure that defines a component cavity; a substrate having an exterior surface and an interior surface opposing the exterior surface; a physiological characteristic sensor element located on the exterior surface of the substrate, the physiological characteristic sensor element including sensor electrodes; a multilayer component stack mounted in the enclosure structure, the multilayer component stack including features and components to provide processing and wireless communication functionality for sensor data obtained in association with operation of the physiological characteristic sensor element, and the multilayer component stack including an active layer, a passive component layer, and a power source component layer; and conductive plug elements located in vias formed through the substrate, each conductive plug element having a first end electrically coupled to one of the sensor electrodes, and having a second end electrically coupled to the multilayer component stack. The substrate encloses the multilayer component stack inside component cavity of the enclosure structure.

In accordance with an embodiment, a method of fabricating physiological characteristic sensor devices involves: forming a conductive circuit pattern overlying a first surface of a base substrate, the conductive circuit pattern electrically coupled to conductive plug elements located in vias formed through the base substrate, the conductive circuit pattern including individual circuit layouts for a plurality of die locations, and the conductive plug elements arranged in a pattern for the plurality of die locations; mounting a plurality of multilayer component stacks to the conductive circuit pattern such that each multilayer component stack is electrically and physically coupled to a respective one of the individual circuit layouts, each multilayer component stack including features and components to provide processing and wireless communication functionality for obtained sensor data; after the mounting, forming an enclosure structure overlying the first surface of the base substrate to individually cover and enclose each of the multilayer component stacks; fabricating physiological characteristic sensor elements overlying a second surface of the base substrate, the second surface opposing the first surface of the base substrate, each physiological characteristic sensor element including sensor electrodes electrically coupled to respective instances of the conductive plug elements, and each physiological characteristic sensor element corresponding to a respective one of the die locations, wherein the fabricating results in a plurality of sensor devices integrated on and carried by the base substrate; and after the fabricating, separating each of the plurality of sensor devices from one another, resulting in a plurality of physically discrete sensor device components.

In accordance with an embodiment, a method of manufacturing physiological characteristic sensor devices involves: assembling a plurality of multilayer component stacks for a plurality of physiological characteristic sensor devices, each multilayer component stack including features and components to provide processing and wireless communication functionality for obtained sensor data; mounting the multilayer component stacks to a conductive circuit pattern formed on a first surface of a base substrate, the conductive circuit pattern electrically coupled to conductive plug elements located in vias formed through the base substrate, the conductive circuit pattern and the conductive plug elements cooperating to form individual circuit layouts for a plurality of die locations, wherein the mounting step electrically and physically couples each multilayer component stack to a respective one of the circuit layouts; after the mounting, affixing an enclosure structure to the first surface of the base substrate to individually cover and enclose each of the multilayer component stacks; fabricating physiological characteristic sensor elements overlying a second surface of the base substrate, the second surface opposing the first surface of the base substrate, each physiological characteristic sensor element including sensor electrodes electrically coupled to respective instances of the conductive plug elements, and each physiological characteristic sensor element corresponding to a respective one of the die locations, wherein the fabricating results in a plurality of sensor devices integrated on and carried by the base substrate; and after the fabricating, separating each of the plurality of sensor devices from one another, resulting in a plurality of physically discrete sensor device components.

In accordance with an embodiment, a method of fabricating a glucose sensor device involves: providing a base substrate comprising conductive plug elements located in vias formed through the base substrate, the conductive plug elements arranged in a pattern corresponding to a die location for the glucose sensor device; forming a conductive circuit pattern for the glucose sensor device, the circuit pattern overlying a first surface of the base substrate, and the circuit pattern electrically coupled to the conductive plug elements; mounting a multilayer component stack to the circuit pattern such that the multilayer component stack is electrically and physically coupled to the circuit pattern, the multilayer component stack including features and components to provide processing and wireless communication functionality for sensor data obtained in association with operation of the glucose sensor device; after the mounting, covering the multilayer component stack with an enclosure structure; fabricating a glucose sensor element overlying a second surface of the base substrate, the second surface opposing the first surface of the base substrate, the glucose sensor element including sensor electrodes electrically coupled to respective instances of the conductive plug elements, wherein the fabricating results in the glucose sensor device integrated on and carried by the base substrate; and after the fabricating, cutting the base substrate to separate the glucose sensor device.

In accordance with an embodiment, a method of manufacturing physiological characteristic sensor devices involves: assembling a plurality of multilayer component stacks for a plurality of physiological characteristic sensor devices, each multilayer component stack including features and components to provide processing and wireless communication functionality for obtained sensor data; mounting the multilayer component stacks into respective component cavities formed in a base substrate; after mounting the multilayer component stacks, affixing a sensor substrate overlying the base substrate to individually cover and enclose each of the multilayer component stacks within their respective component cavities, wherein the sensor substrate comprises conductive plug elements located in vias formed through the sensor substrate, and wherein affixing the sensor substrate electrically couples the conductive plug elements to the multilayer component stacks; fabricating physiological characteristic sensor elements overlying a surface of the sensor substrate, each physiological characteristic sensor element including sensor electrodes electrically coupled to respective instances of the conductive plug elements formed through the sensor substrate, wherein the fabricating results in a plurality of sensor devices integrated on and carried by the sensor substrate; and after the fabricating, separating each of the plurality of sensor devices from one another, resulting in a plurality of physically discrete sensor device components.

This summary is provided to introduce a selection of concepts in a simplified form that are further described below in the detailed description. This summary is not intended to identify key features or essential features of the claimed subject matter, nor is it intended to be used as an aid in determining the scope of the claimed subject matter.

BRIEF DESCRIPTION OF THE DRAWINGS

A more complete understanding of the subject matter may be derived by referring to the detailed description and claims when considered in conjunction with the following figures, wherein like reference numbers refer to similar elements throughout the figures.

DETAILED DESCRIPTION

Figure 1:
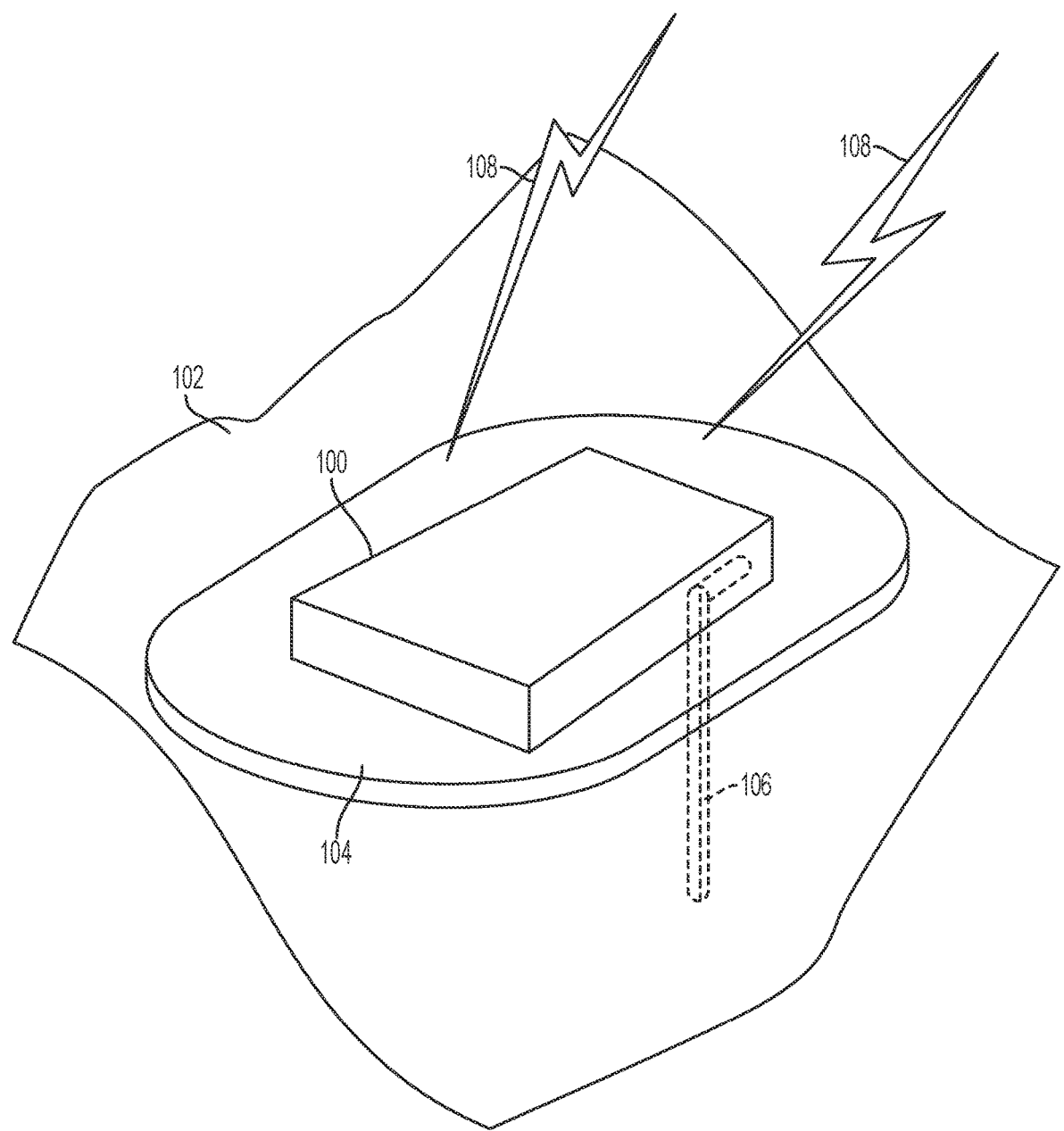
FIG. 1 is a perspective view of a simplified representation of a physiological characteristic sensor device as deployed for use.

The following detailed description is merely illustrative in nature and is not intended to limit the embodiments of the subject matter or the application and uses of such embodiments. As used herein, the word "exemplary" means "serving as an example, instance, or illustration." Any implementation described herein as exemplary is not necessarily to be construed as preferred or advantageous over other implementations. Furthermore, there is no intention to be bound by any expressed or implied theory presented in the preceding technical field, background, brief summary or the following detailed description.

In addition, certain terminology may also be used in the following description for the purpose of reference only, and thus are not intended to be limiting. For example, terms such as "upper", "lower", "above", and "below" refer to directions in the drawings to which reference is made. Terms such as "front", "back", "rear", "side", "outboard", and "inboard" describe the orientation and/or location of portions of the component within a consistent but arbitrary frame of reference which is made clear by reference to the text and the associated drawings describing the component under discussion. Such terminology may include the words specifically mentioned above, derivatives thereof, and words of similar import. Similarly, the terms "first", "second", and other such numerical terms referring to structures do not imply a sequence or order unless clearly indicated by the context.

The subject matter described here relates to a physiological characteristic sensor device package, and a related manufacturing process. The non-limiting exemplary embodiment described below relates to a continuous glucose sensor of the type used by diabetic patients. It should be appreciated, however, that the sensor device structure and configuration, and the related fabrication techniques presented here need not be limited to use with glucose sensors and, indeed, the concepts and technology described with reference to a glucose sensor could also be used with other medical devices, other sensor types, other medical components or supplies, and the like.

A glucose sensor of the type described here may be realized as an electrochemical sensor that employs the glucose oxidase enzyme. Sensors that use glucose oxidase to effect a reaction of glucose and oxygen are known, and such glucose sensors will not be described in detail here. For the sake of brevity, conventional aspects and technology related to glucose sensors and glucose sensor fabrication may not be described in detail here. In this regard, known and/or conventional aspects of glucose sensors and their manufacturing may be of the type described in, but not limited to, U.S. Pat. Nos. 6,892,085, 7,468,033, and 9,295,786 (which are incorporated by reference herein).

Current glucose sensor systems have two components: the glucose sensor component and the wireless transmitter component. The sensor is typically replaced once every several days, and the transmitter is typically removed from the sensor and recharged every three days. Moreover, the transmitter is usually replaced about once per year. In accordance with the exemplary use case described here, the transmitter component is compatible with an insulin pump device to support wireless communication of glucose sensor data from the glucose sensor to the pump device.

In contrast to conventional glucose sensor systems, the exemplary embodiment presented here integrates the sensor and transmitter into one disposable device package that is easy to deploy and manage by the patient. In certain implementations, the combined sensor/transmitter device package requires no patient intervention over a desired period of continuous use (e.g., more than a day, a week, up to 30 days for acute use, or any suitable length of time). In this regard, after deploying the sensor/transmitter device package, there is no need to recharge the device, and there is no need to connect or disconnect multiple components. Instead, the patient simply wears the sensor/transmitter device package for the desired number of days, removes and discards it, and replaces it with a new one.

In accordance with the exemplary fabrication process presented here, waferscale technology is utilized to build a large number of sensor/transmitter device packages from a substrate, such as a semiconductor wafer. As one non-limiting example, up to 184 individual device packages can be fabricated using one ten-inch semiconductor wafer as the foundation. Each device is realized as a discrete stack of functional layers, and each stack is coupled to the foundation wafer. A cap or "lid" structure is fabricated from another substrate, such as another semiconductor wafer. The cap structure is coupled overlying the foundation wafer in a way that creates enclosures for the individual device packages. Thereafter, the device packages are cut or otherwise separated into discrete sensor/transmitter components.

Referring now to the drawings, FIG. 1 is a perspective view of a simplified representation of a physiological characteristic sensor device 100 as deployed for use on the skin 102 of a patient. The sensor device 100 is affixed to the skin 102 by way of an adhesive patch 104, which holds the sensor device 100 in position with its physiological characteristic sensor element 106 inserted into the skin 102. As mentioned above, the sensor device 100 is manufactured using waferscale fabrication technology on a common substrate with multiple sensor devices 100. The sensor device 100 includes the features, components, devices, and elements necessary to support both sensor-related functionality and wireless transmitter functionality. The wireless links 108 shown in FIG. 1 schematically illustrate that the sensor device 100 is capable of supporting wireless data communication with one or more compatible devices, and without requiring another companion device or component connected thereto.

Figure 2:
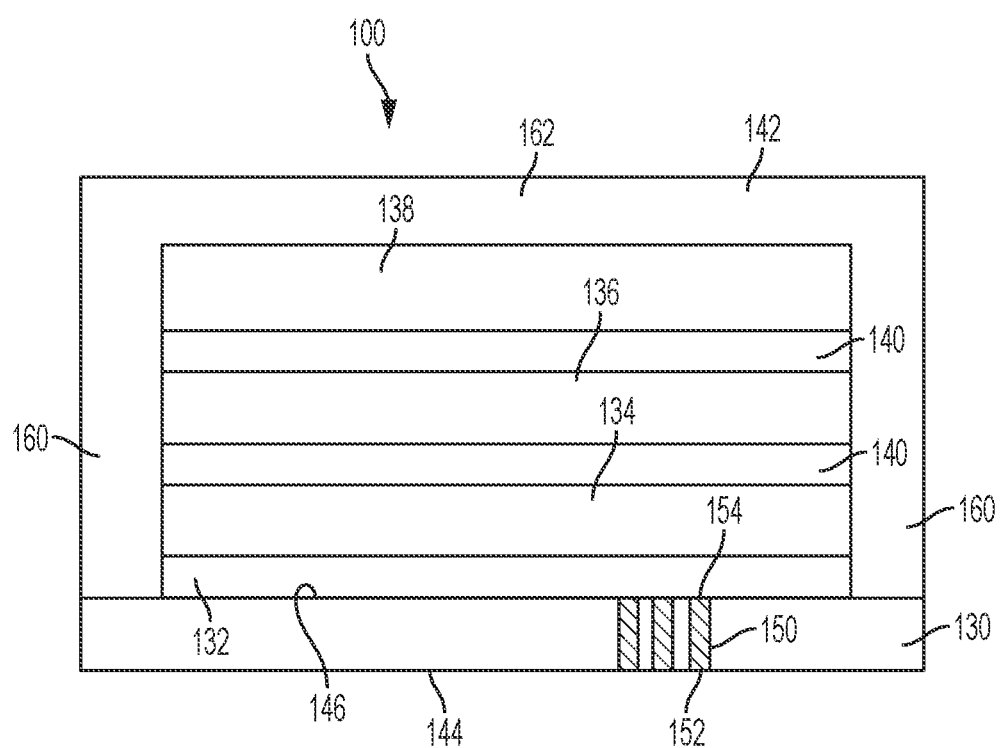
FIG. 2 is a schematic cross-sectional view of an exemplary embodiment of the physiological characteristic sensor device shown in FIG. 1.

FIG. 2 is a schematic cross-sectional view of an exemplary embodiment of the sensor device 100 shown in FIG. 1. For simplicity and ease of illustration, the adhesive patch 104 and the sensor element 106 are not shown in FIG. 2. Moreover, FIG. 2 exaggerates the size of the illustrated features to make them easier to distinguish from one another. The illustrated embodiment of the sensor device 100 generally includes, without limitation: a base substrate 130; a conductive circuit pattern 132; a passive component layer 134; an active layer 136; a power source component layer 138; an interconnect arrangement 140; and an enclosure structure 142. The passive component layer 134, the active layer 136, the power source component layer 138, and the interconnect arrangement 140 together form a multilayer component stack for the sensor device 100.

The base substrate 130 is formed from an appropriate material that accommodates waferscale manufacturing. In this regard, the base substrate 130 may be formed from (or include) any of the following materials, without limitation: a semiconductor material such as silicon; a glass material; a ceramic material; sapphire material; polymer material; plastic material; or a composite material. The base substrate 130 has an exterior surface 144 and an interior surface 146 opposing the exterior surface 144. Referring to FIG. 1, the sensor element 106 is located on the exterior surface 144, and it extends from the exterior surface 144 when deployed for insertion in the skin 102 of the patient.

The conductive circuit pattern 132 is formed overlying the interior surface 146 of the base substrate 130 (preferably in accordance with the manufacturing process described in more detail below). In certain exemplary embodiments, the circuit pattern 132 is formed directly on the interior surface 146 to provide the desired electrical paths, connections, and traces for the component layers of the sensor device 100. Accordingly, the circuit pattern 132 can be considered to be an integral feature of the base substrate 130 in some embodiments. It should be appreciated that FIG. 2 simplistically depicts the circuit pattern 132 as a continuous blocked layer merely to demonstrate the location of the circuit pattern 132 relative to the other components and features of the sensor device 100.

Electrically conductive plug elements 150 are located in respective vias that are formed through the base substrate 130. The illustrated embodiment employs three plug elements 150, although the exact number may vary from one implementation to another, depending on the electrical requirements of the sensor element 106. Each plug element 150 defines an electrically conductive path between the exterior surface 144 and the interior surface 146 of the base substrate 130. For this particular embodiment, each plug element 150 has a first end 152 electrically coupled to one of the three sensor electrodes of the sensor element 106 (not shown in FIG. 1 or FIG. 2; see FIG. 11), and a second end 154 electrically coupled to the circuit pattern 132. Accordingly, the plug elements 150 electrically connect the sensor electrodes to one or more of the internal component layers of the sensor device 100.

As mentioned above, the multilayer component stack of the sensor device 100 includes at least the following items: the passive component layer 134; the active layer 136; the power source component layer 138; and the interconnect arrangement 140. In practice, additional component layers can be utilized, and/or two or more of the component layers listed above can be integrated into a single component layer if so desired. The multilayer component stack is carried on the base substrate 130, and it is physically and electrically connected to the conductive circuit pattern 132. The multilayer component stack includes various features, components, elements, and/or devices that cooperate to provide the processing and wireless communication functionality for sensor data that is obtained in association with the operation of the sensor device 100. To this end, the interconnect arrangement 140 is suitably configured and fabricated to electrically and physically couple together the passive component layer 134, the active layer 136, and the power source component layer 138 as needed. It should be appreciated that some or all of the circuit pattern 132 may also form a part of the interconnect arrangement 140. In certain implementations, the interconnect arrangement 140 can include: electrical traces; conductive interlayer elements; solder balls or tabs; conductive pads; electrically conductive adhesive; dielectric material, elements, or layers; etc.

For this particular embodiment, the passive component layer 134 is electrically and physically coupled to the circuit pattern 132 as the first layer of the multilayer component stack. In other words, the passive component layer 134 is the layer that is nearest the base substrate 130. The passive component layer 134 may also be electrically coupled to one or more features of the active layer 136 and/or to one or more features of the power source component layer 138. The passive component layer 134 includes passive electrical elements, components, or devices including, without limitation: an antenna element utilized for wireless data communication; discrete components (e.g., resistors, inductors, capacitors); conductive traces. In some embodiments, the passive component layer 134 may include passive electrical elements integrated with active components. The passive component layer 134 is suitably configured to support wireless transmission functions, impedance matching, and voltage regulation, and to otherwise support various features and functions that are associated with the operation of the active layer 136. The passive component layer 134 is preferably arranged as the first or last layer of the stack to improve the efficiency and operation of the wireless antenna. Although the passive component layer 134 includes the wireless antenna in this embodiment, the antenna can be placed on any other component layer if so desired. Moreover, an implementation could utilize multiple antennas located on different component layers.

For this particular embodiment, the active layer 136 is electrically and physically coupled to the passive component layer 134 as the second layer of the multilayer component stack. The active layer 136 may also be electrically coupled to one or more areas of the circuit pattern 132 and/or to one or more features of the power source component layer 138. In certain embodiments, the active layer 136 includes or is realized as a system on a chip (SoC) device that is programmed in accordance with the desired feature set and functionality of the sensor device 100. As one non-limiting example, the active layer 136 can include a programmable system-on-chip device having a microprocessor, a BLUETOOTH Low Energy (BLE) wireless radio and subsystem, programmable analog and digital features, memory, power management, and other features and functions integrated therein.

For this particular embodiment, the power source component layer 138 is electrically and physically coupled to the active layer 136 as the third layer of the multilayer component stack. In other words, the power source component layer 138 is the layer that is farthest from the base substrate 130. The power source component layer 138 may also be electrically coupled to one or more areas of the circuit pattern 132 and/or to one or more features of the passive component layer 134. In certain embodiments, the power source component layer 138 includes or is realized as a plurality of solid state battery components configured in a stacked arrangement. The illustrated example implements the power source component layer 138 with only one solid state battery device. The power source component layer 138 may include a wirelessly rechargeable battery or a disposable single-use battery having a shelf life and capacity that is sufficient for the intended application.

The enclosure structure 142 is coupled to the base substrate 130 to enclose the interior surface 146 of the base substrate 130, the conductive circuit pattern 132, and the multilayer component stack. As explained in more detail below, the enclosure structure 142 is fabricated, formed, and/or installed over the base substrate during bulk processing of a plurality of sensor devices 100. Thereafter, the encapsulated individual sensor devices 100 are separated from one another, such that each one resembles the configuration shown in FIG. 2. In accordance with an exemplary embodiment, the enclosure structure 142 is formed from a second substrate such that the enclosure structure 142 includes or defines a plurality of sidewalls 160 and a lid 162 that is integrally formed with the sidewalls 160. Although not fully shown in FIG. 2, the enclosure structure 142 resembles a cap overlying and covering the internal components of the sensor device 100, with the base substrate 130 serving as the bottom of the "box" depicted in FIG. 2.

In an alternative embodiment, the enclosure structure 142 is formed from a compression molded material overlying the base substrate 130 and the multilayer component stack, wherein the molded material is cut (while separating the plurality of sensor devices 100 from one another) to define the individual enclosure structure 142 for each sensor device. In another alternative embodiment, the enclosure structure 142 is formed from an overmolded material overlying the base substrate 130 and the multilayer component stack, wherein the overmolded material is cut (while separating the sensor devices 100) to define the individual enclosure structure 142 for each sensor device. In this regard, the compression molded or overmolded material may be, without limitation: epoxy; polymer; or co-polymer material.

Figure 3:
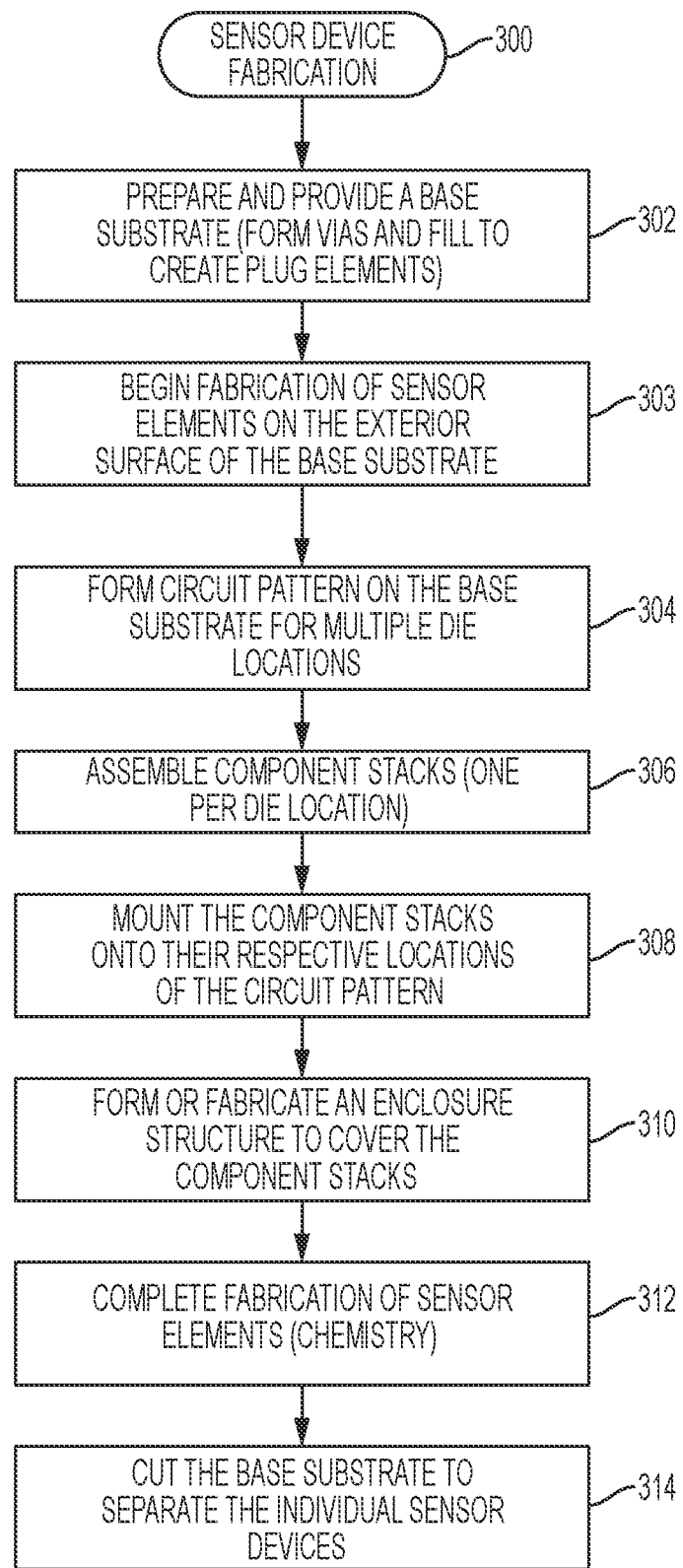
FIG. 3 is a flow chart that illustrates an exemplary embodiment of a sensor device fabrication process.

FIG. 3 is a flow chart that illustrates an exemplary embodiment of a sensor device fabrication process 300 that can be employed to manufacture the sensor device 100. The process 300 will be described with reference to FIGS. 4-12. It should be appreciated that an embodiment of the process 300 may include any number of additional or alternative tasks, the tasks shown in FIG. 3 need not be performed in the illustrated order, and the process 300 may be incorporated into a more comprehensive procedure or process having additional functionality not described in detail herein. Moreover, one or more of the tasks shown in FIG. 3 could be omitted from an embodiment of the process 300 as long as the intended overall functionality remains intact.

The fabrication process 300 begins by preparing and providing a base substrate (e.g., a wafer) to serve as the foundation for the creation of a plurality of physiological characteristic sensor devices (task 302). In accordance with one non-limiting embodiment, the base substrate is realized using a ten-inch diameter silicon-based wafer that is about 0.1 to 1.1 mm thick. In practice, a ten-inch wafer can be used to fabricate about 184 sensor devices, wherein the die size for each sensor device is approximately 10.5 mm by 10.5 mm square. Of course, any suitable diameter and thickness for the substrate can be utilized, and the size of each die location can be selected to accommodate the needs of the particular embodiment. Task 302 may include the following process steps: preparing the base substrate wafer; forming a plurality of vias (through holes) in the base substrate, wherein the vias are arranged in a desired pattern for the plurality of die locations; and filing the vias with an electrically conductive material to create corresponding conductive plug elements in the base substrate. In this regard, task 302 can leverage conventional technologies and processes related to patterning, etching, material deposition, and the like. It should be appreciated that task 302 can be performed by a vendor or manufacturer of wafer substrates, such that the prepared base substrate (with conductive plugs formed therein) can be delivered to the sensor device manufacturer for further handling in the manner described below. Alternatively, task 302 can be performed by the sensor device manufacturer as an integrated part of the overall fabrication process.

Figure 4:
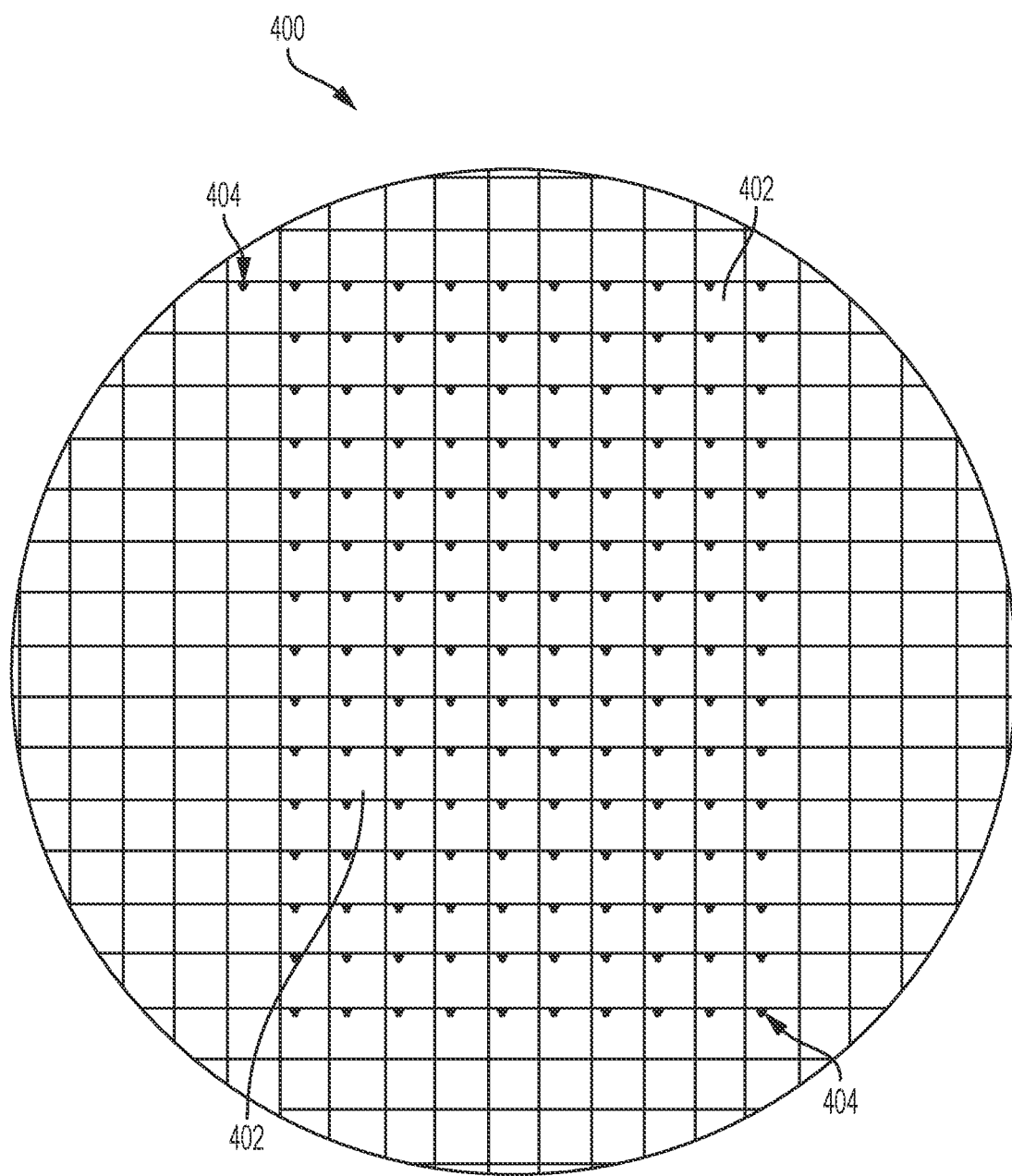
FIG. 4 is a plan view of a base substrate suitable for use in manufacturing a plurality of physiological characteristic sensor devices.

The number of conductive plugs per die location can vary, depending on the design and operating requirements of the sensor device. The exemplary embodiment described here is designed to accommodate glucose sensors, each having three electrodes. Accordingly, each die location of the base substrate includes three conductive plugs. In this regard, FIG. 4 is a plan view of a base substrate 400 suitable for use in manufacturing a plurality of glucose sensor devices. FIG. 4 depicts the state of the base substrate 400 after completion of task 302 in that each die location of interest includes vias and conductive plugs formed therein. In FIG. 4, the squares represent the die locations 402, and the small dots in the die locations 402 correspond to the conductive plugs 404 (three conductive plugs 404 per die location 402).

Referring again to FIG. 3, the sensor device fabrication process 300 continues by beginning the fabrication of glucose sensor elements overlying an exterior surface of the base substrate (task 303). More specifically, the "exterior surface" will eventually become the outer exposed surface of the sensor device (see FIG. 10 and the related description of task 312 below). Task 303 is associated with certain process steps that define the physical and electrical features of the glucose sensor elements. Notably, the chemistry related steps associated with the creation of the glucose sensor elements are not performed during task 303. To this end, task 303 is performed such that each glucose sensor element includes sensor electrodes coupled to respective instances of the conductive plug elements located in the corresponding die location. Accordingly, one sensor element is fabricated for each die location. For the exemplary embodiment described here, a sensor element pattern is defined and formed directly on the surface of the base substrate 400, resulting in a plurality of glucose sensor devices integrated on, and carried by, the base substrate 400. Task 303 can leverage conventional techniques and methodologies for creating physiological sensor elements of the type described here. In this regard, the following process steps can be performed during task 303: form a base polyimide layer; metallization; form an intermediate polyimide layer; etching; and form a top polyimide layer.

The sensor device fabrication process 300 continues by forming a conductive circuit pattern overlying a first surface of the base substrate (task 304). The circuit pattern is fabricated on the major surface of the base substrate that eventually becomes the interior surface of the sensor device (see FIG. 2). For the exemplary embodiment described here, task 304 forms the circuit pattern directly on the surface of the base substrate using conventional patterning, metallization, etching, and/or other process technologies. The circuit pattern includes individual circuit layouts (which are identical) for the different die locations. The circuit pattern is configured, arranged, and formed such that it is electrically coupled to the conductive plug elements. Thus, the conductive plug elements and the circuit pattern are cooperatively designed and arranged in consistent and compatible patterns for the plurality of die locations. The circuit layout for each die location (i.e., for each sensor device to be fabricated) includes electrically conductive traces, contact pads, and features designed for compatibility with the multilayer component stack to be mounted to the die location.

Figure 5:
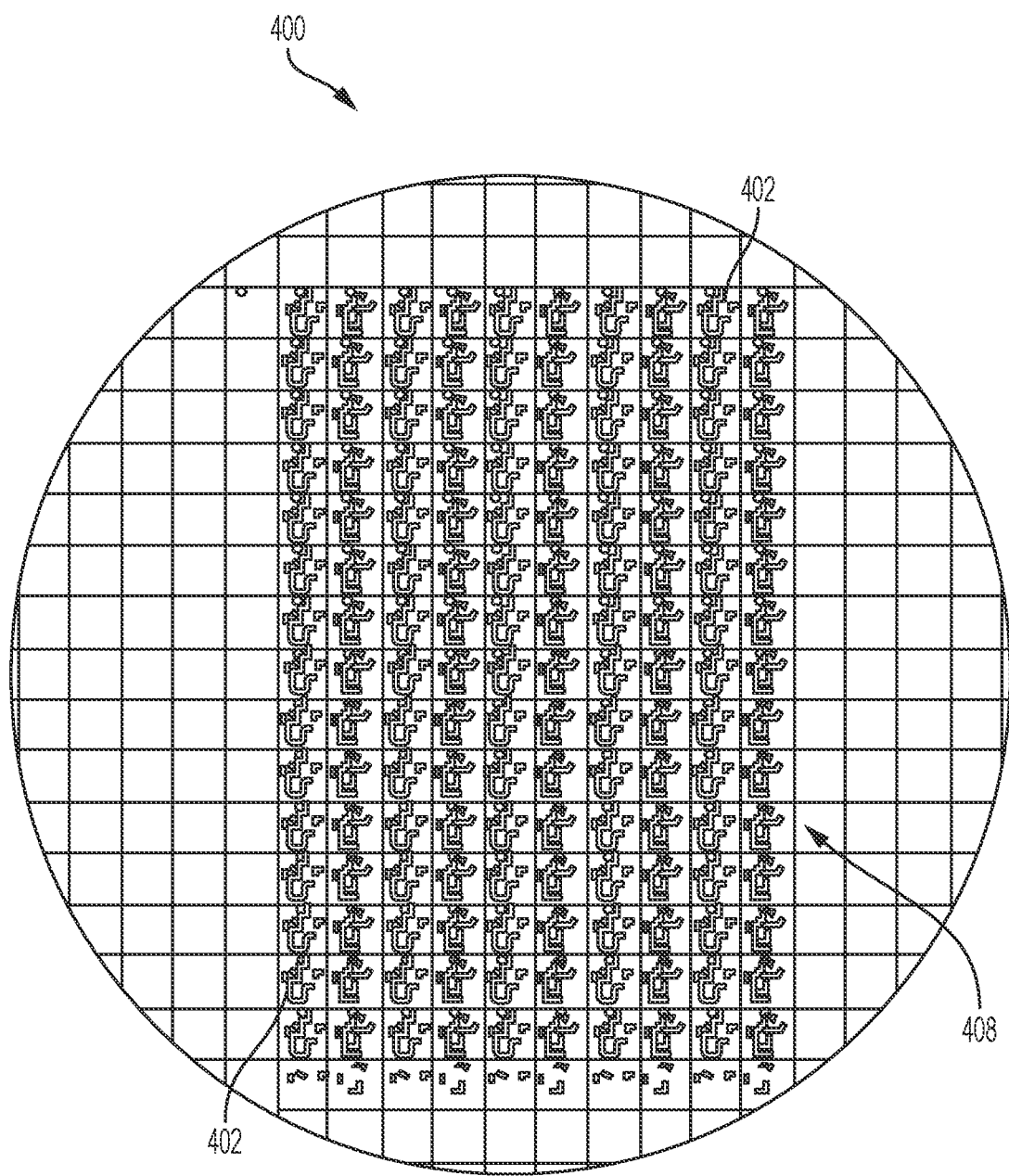
FIG. 5 is a plan view of the base substrate having a conductive circuit pattern formed thereon.
Figure 6:
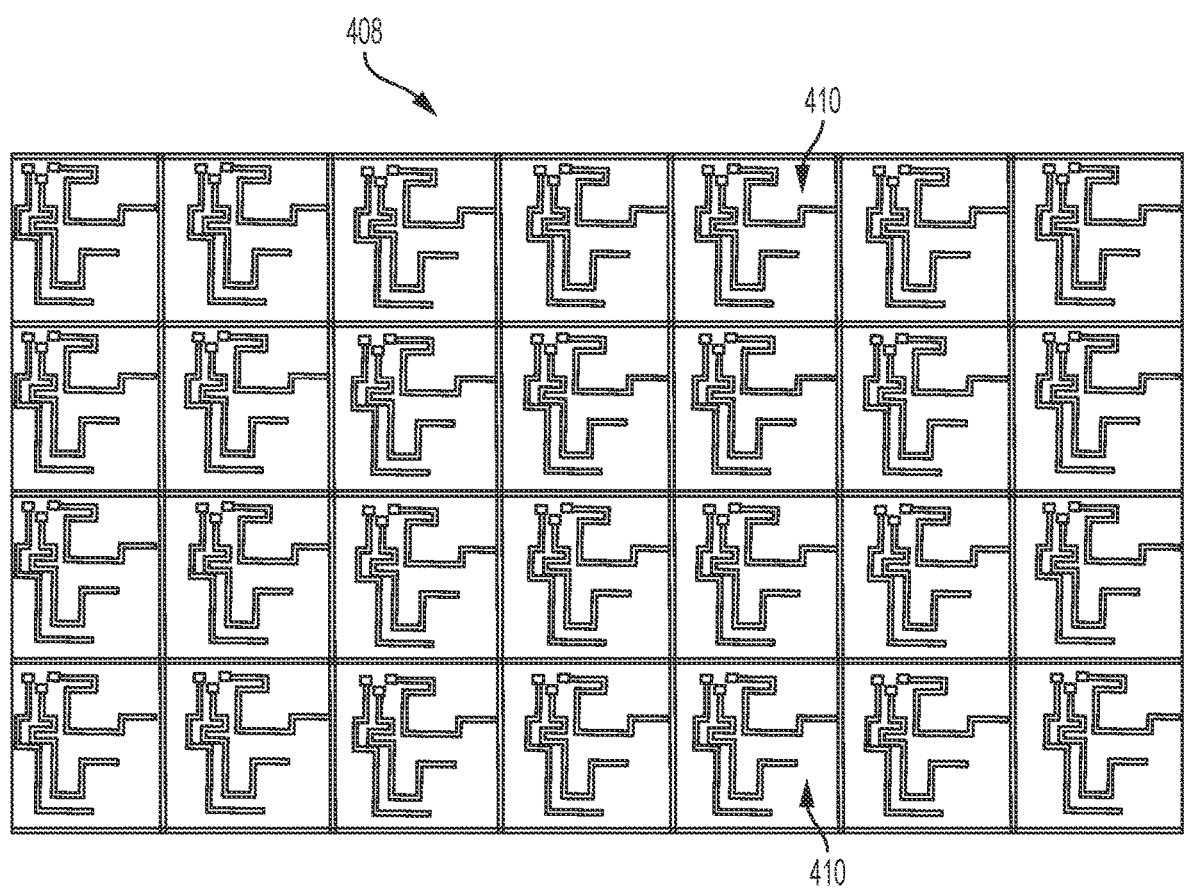
FIG. 6 is a detailed plan view of the conductive circuit pattern, showing a layout for a plurality of die locations of the base substrate.

FIG. 5 is a plan view of the base substrate 400 after having a conductive circuit pattern 408 formed thereon. In this context, the circuit pattern 408 includes a repetitive pattern of discrete circuit layouts, one for each die location. In this regard, FIG. 6 is a detailed plan view of the conductive circuit pattern 408, showing an exemplary embodiment of a circuit layout 410 for a plurality of die locations of the base substrate 400. As depicted in FIG. 6, the same circuit layout 410 (as defined by the overall circuit pattern 408) is concurrently formed for a plurality of die locations. Notably, the circuit layout 410 for each die location is electrically connected to the three conductive plugs 404 that reside in that particular die location.

Referring again to FIG. 3, the sensor device fabrication process 300 continues by assembling or obtaining (if pre-assembled) a plurality of multilayer component stacks for the glucose sensor devices (task 306). As described above, each multilayer component stack is fabricated from a plurality of individual and distinct device/component layers that cooperate with one another to provide the processing and wireless communication functionality for the obtained glucose sensor data. Accordingly, task 306 may involve a number of assembly steps that establish the necessary electrical and physical connections between the various component layers (e.g., the passive component layer, the active layer, and the power source component layer). In practice, therefore, task 306 may involve soldering, reflowing, bonding, and/or conductive epoxying as needed to fabricate each multilayer component stack from its constituent parts.

Figure 7:
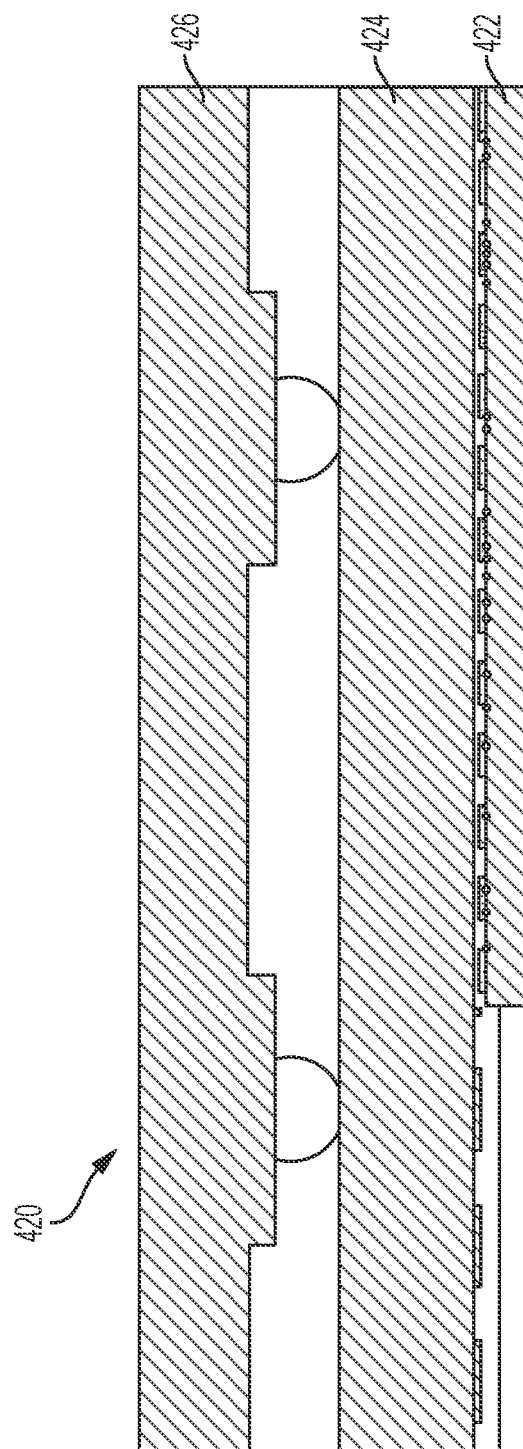
FIG. 7 is a schematic elevation view of an exemplary embodiment of a multilayer component stack suitable for use with a physiological characteristic sensor device.

FIG. 7 is a schematic elevation view of an exemplary embodiment of a multilayer component stack 420 that is suitable for use with a glucose sensor device. FIG. 7 depicts the multilayer component stack 420 after it has been assembled together from the three separate component layers, as described above. For this particular embodiment, the multilayer component stack 420 includes a passive component layer 422, an active layer 424, and a power source component layer 426 in a stacked arrangement. The multilayer component stack 420 also includes an interconnect arrangement (not separately numbered in FIG. 7), which can be realized with conductive traces, solder balls, interlayer conductive elements, etc. For the example described here, 184 instances of the multilayer component stack 420 are prepared for attachment to the base substrate 400.

Figure 8:
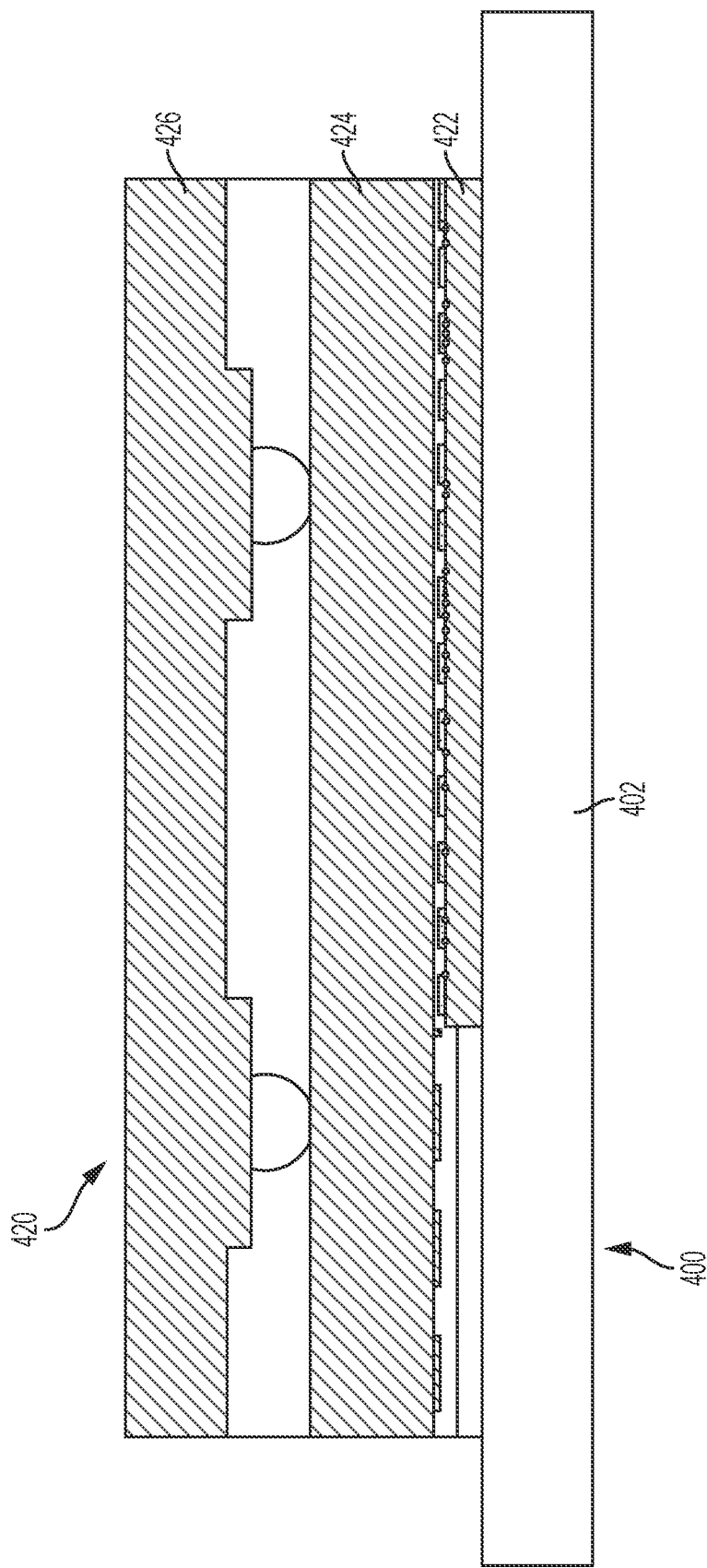
FIG. 8 is a schematic elevation view of an assembly that includes the multilayer component stack shown in FIG. 7 mounted to the base substrate.

Next, the assembled multilayer component stacks are mounted and affixed to respective die locations of the base substrate (task 308). More specifically, the component stacks are mounted to the conductive circuit pattern that has been formed on the base substrate, such that each component stack is physically and electrically coupled to a respective one of the individual circuit layouts. Task 308 may utilize conventional "pick and place" technologies and equipment, and may involve soldering, reflowing, bonding, and/or conductive epoxying as needed to connect each multilayer component stack to its designated area of the base substrate. FIG. 8 is a schematic elevation view of an assembly that includes the multilayer component stack 420 mounted to one die location 402 of the base substrate 400. After the completion of task 308, each usable die location 402 of the base substrate 400 will be populated with an instantiation of the multilayer component stack 420.

The sensor device fabrication process 300 continues by forming, fabricating, or installing an enclosure structure overlying the surface of the base substrate, to individually cover and enclose each of the mounted component stacks (task 310). In accordance with certain embodiments, the enclosure structure is fabricated from a second substrate (wafer) by forming a pattern of cavities in the second substrate. The material that forms the second substrate and the material that forms the base substrate may be the same, or different. For example, the second substrate can be formed from a polymer or plastic material. The cavities can be etched or otherwise formed in an arrangement that is designed and configured to individually enclose each of the multilayer component stacks. After the cavities are created, the surface of the second substrate resembles a waffle, with an array of pockets that are shaped and sized to accommodate the component stacks. Thus, the second substrate can be attached overlying the surface of the base substrate to "seal" each component stack. As a result, each component stack is individually covered and enclosed within a respective cavity of the second substrate. In certain embodiments, the second substrate is attached to the base substrate using epoxy, a wafer bond material, or the like.

Figure 9:
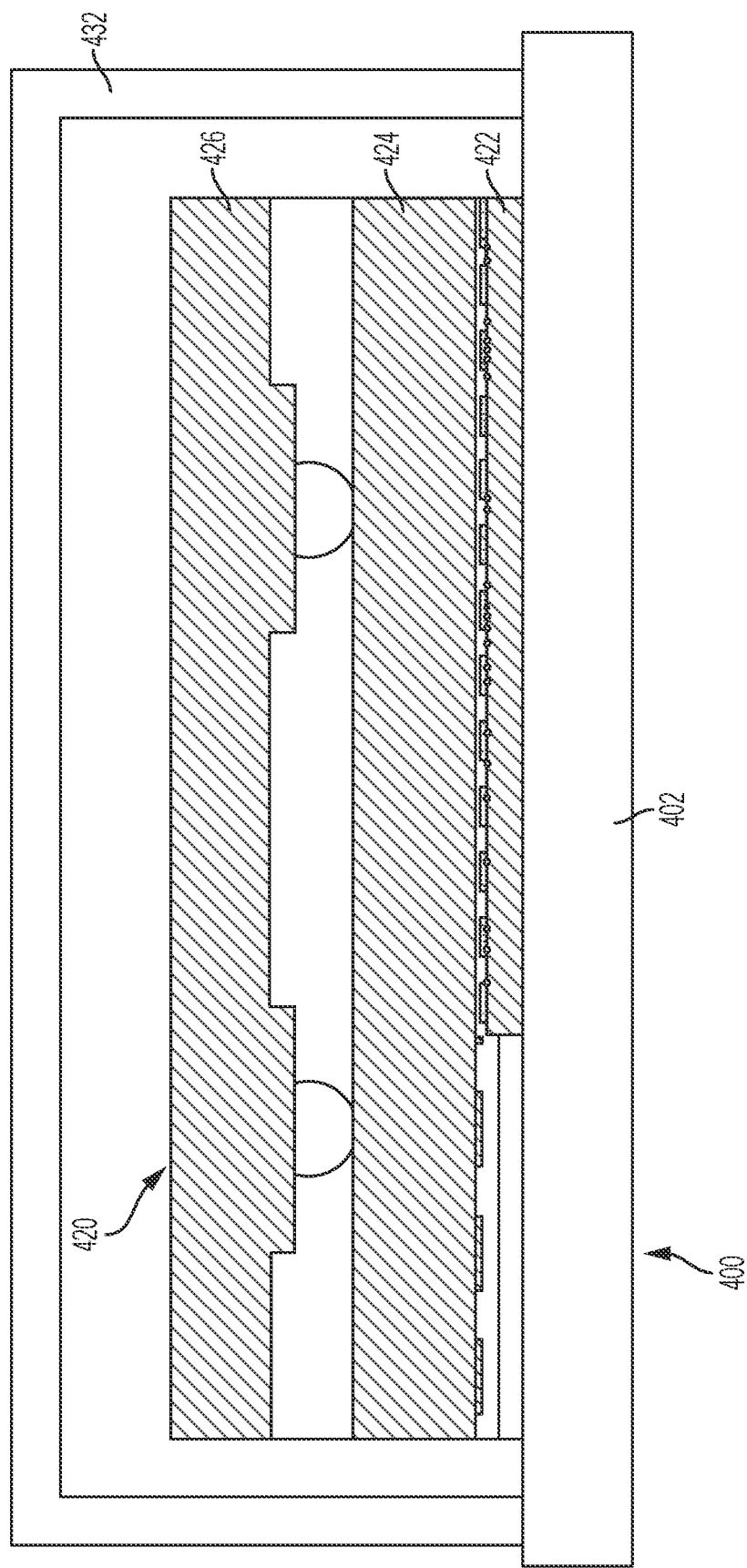
FIG. 9 is a schematic elevation view of an assembly that includes the multilayer component stack shown in FIG. 7, the base substrate, and an enclosure structure.
Figure 10:
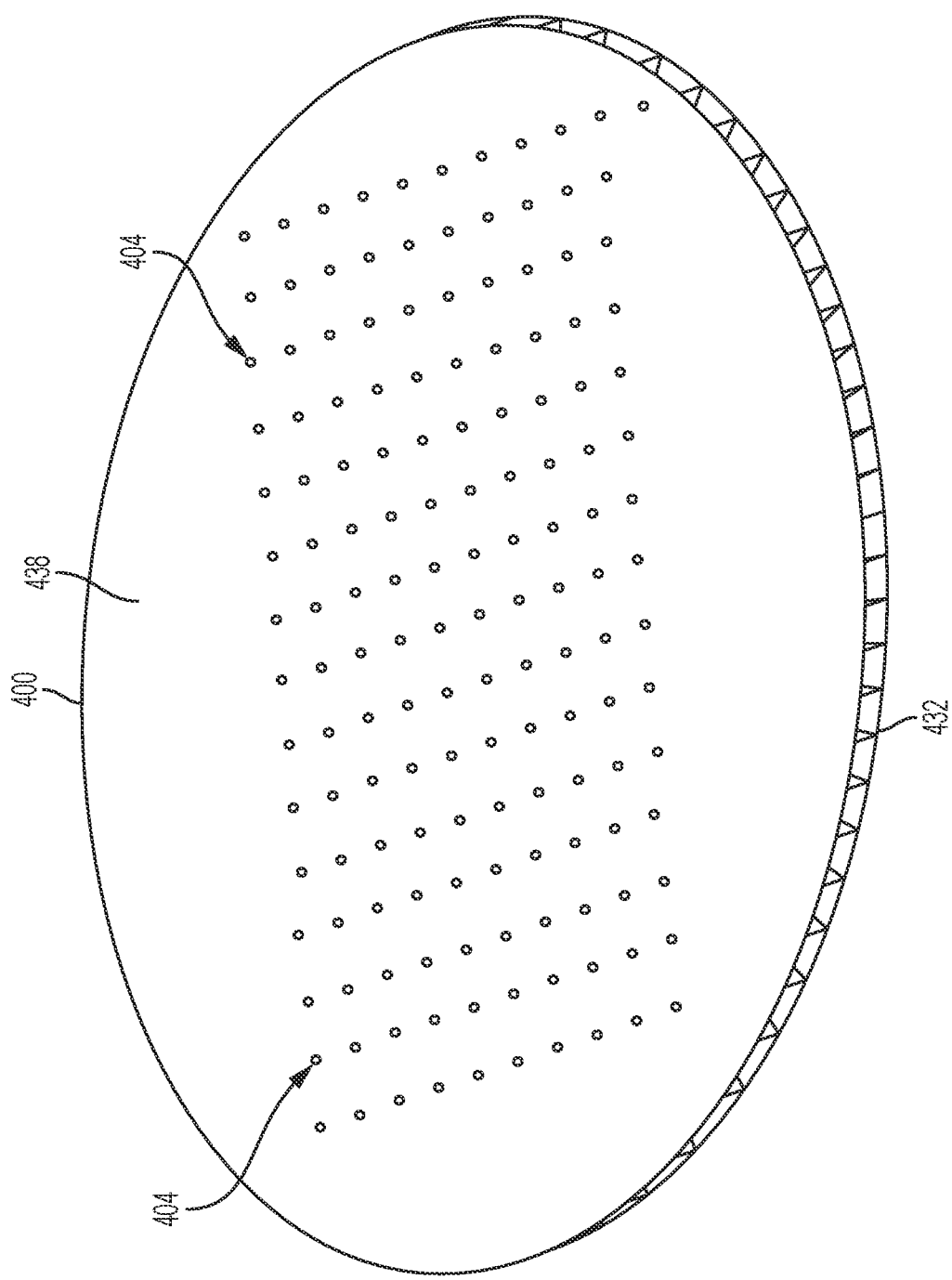
FIG. 10 is a perspective view of an assembly that includes the enclosure structure affixed to the base substrate.

FIG. 9 is a schematic elevation view of an assembly that includes the multilayer component stack 420, a portion of the base substrate 400, and a portion of an enclosure structure 432 overlying the component stack 420. FIG. 9 schematically depicts the enclosure structure 432 as a lid with sidewalls (as described above with reference to FIG. 2). FIG. 9 also shows an exaggerated amount of space around the component stack 420—in practice, the fit of the enclosure structure 432 may be much tighter that that shown in the figure. FIG. 10 is a perspective view of an assembly that includes a waferscale enclosure structure 432 affixed to the base substrate 400 (see FIG. 4, which depicts the base substrate 400 by itself). Notably, the waferscale enclosure structure 432 is shaped and sized in accordance with the overall shape of the base substrate 400 for compatibility. Thus, the enclosure structure 432 resembles a cap or lid for the entirety of the base substrate 400 at this point in the fabrication process 300.

As described previously, an enclosure structure for the base substrate can also be formed by compression molding an appropriate material onto and over the base substrate and the multilayer component stacks. Similarly, an enclosure structure for the base substrate can be formed by overmolding an appropriate material onto and over the base substrate and the component stacks. Molding a material over the base substrate serves to encapsulate and insulate all of the component stacks, and represents a practical alternative to creating a cap/lid structure from a second substrate.

Referring again to FIG. 3, the sensor device fabrication process 300 continues by completing the fabrication of the glucose sensor elements overlying the exterior surface of the base substrate (task 312). The exterior surface 438 is the major surface depicted in FIG. 10; the interior surface of the base substrate (hidden from view) has been covered by the enclosure structure 432. Task 312 completes the process started at task 303 by performing one or more steps associated with the creation of the desired chemistry stack for the glucose sensor elements.

Figure 11:
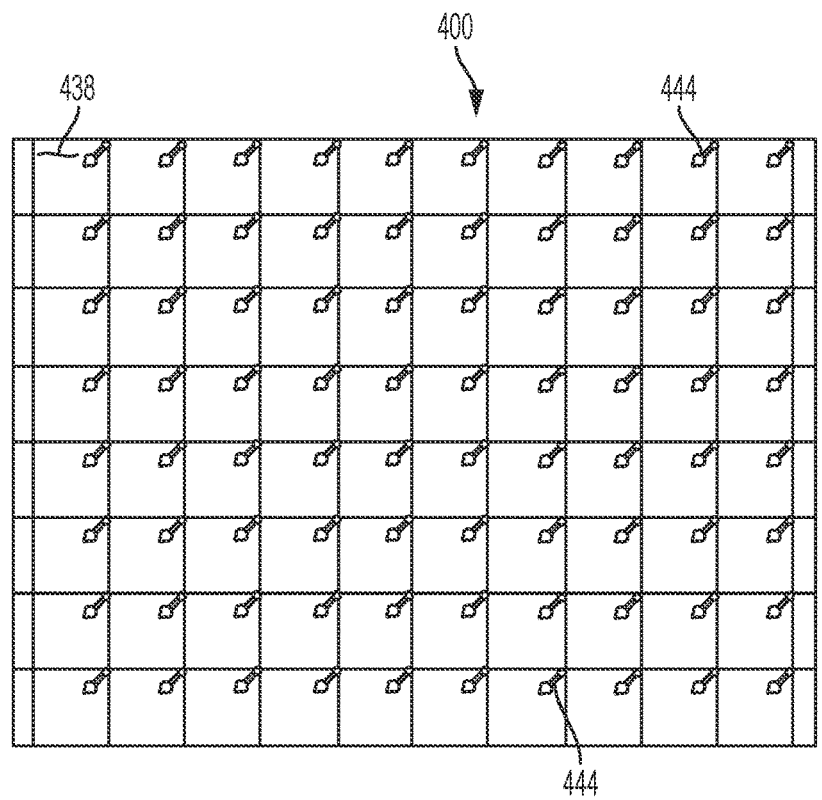
FIG. 11 is a plan view that shows a portion of the exterior surface of the base substrate having sensor elements formed thereon.
Figure 12:
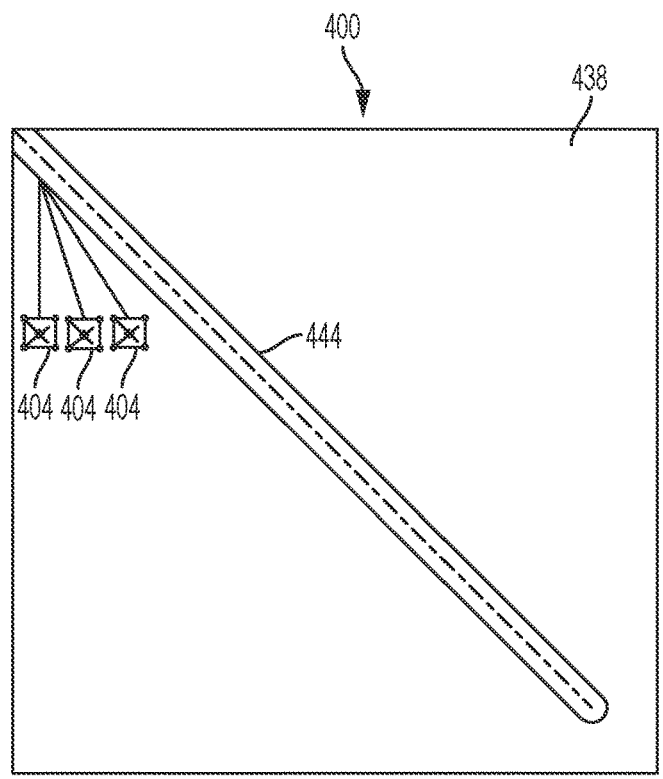
FIG. 12 is a detailed plan view of an exemplary embodiment of one sensor element formed on the exterior surface of the base substrate.

FIG. 11 is a plan view that shows a portion of the exterior surface 438 of the base substrate 400. As shown, the exterior surface 438 includes sensor elements 444 formed thereon. Each die location 402 of interest includes a sensor element 444 located therein. FIG. 12 is a detailed plan view of an exemplary embodiment of one sensor element 444 formed on the exterior surface 438 of the base substrate 400. As depicted in FIG. 12 the electrodes of the sensor element 444 are electrically connected to the conductive plugs 404 by way of conductive traces or features, which are preferably fabricated concurrently with fabrication of the sensor element 444. It should be appreciated that the shape, size, layout, and arrangement of the sensor elements 444 can vary, as appropriate to the particular embodiment, application, sensor type, etc.

In alternative embodiments that utilize a second substrate for the enclosure structure, the sensor elements can be fabricated on the exterior surface of the second substrate (instead of the exterior surface of the base substrate as described above). In such alternative embodiments, conductive plugs are formed in the second substrate to facilitate electrical coupling of the sensor electrodes to conductive pads, interconnect features, or a component layer.

In accordance with an alternative implementation, the sensor devices can be fabricated in the following manner. A waferscale base substrate that resembles a round "waffle" with component cavities corresponding to die locations (as described above for the enclosure structure fabricated from a second substrate) is created or provided. The cavities resemble uncovered boxes or enclosures for the multilayer component stacks. The multilayer component stacks and associated conductive interconnect arrangements are inserted and mounted in their respective component cavities. Thereafter, a waferscale sensor cap or lid substrate is affixed overlying the base substrate to individually cover and enclose each of the multilayer component stacks within their respective component cavities, and to establish electrical connections between the conductive plugs and corresponding features of the multilayer component stacks. As mentioned in the preceding paragraph, in some embodiments the lid substrate includes the sensor elements formed thereon. In alternative embodiments, the sensor elements are fabricated on the exposed surface of the lid substrate after it is attached to the base substrate.

The sensor device fabrication process 300 continues by separating the plurality of sensor devices from one another, by cutting, dicing, or otherwise treating the base substrate in an appropriate manner (task 314). In this regard, task 314 may utilize chemical, laser, or saw separation methodologies to create singulated sensor devices from the waferscale assembly. The particular separation methodology utilized during task 314 can be selected for compatibility with the material used for the base substrate, the technique and composition used to create the enclosure substrate, etc. Task 314 results in a plurality of physically discrete sensor device components. At this time, the sensor device components are ready for final assembly and packaging if so desired.

Figure 13:
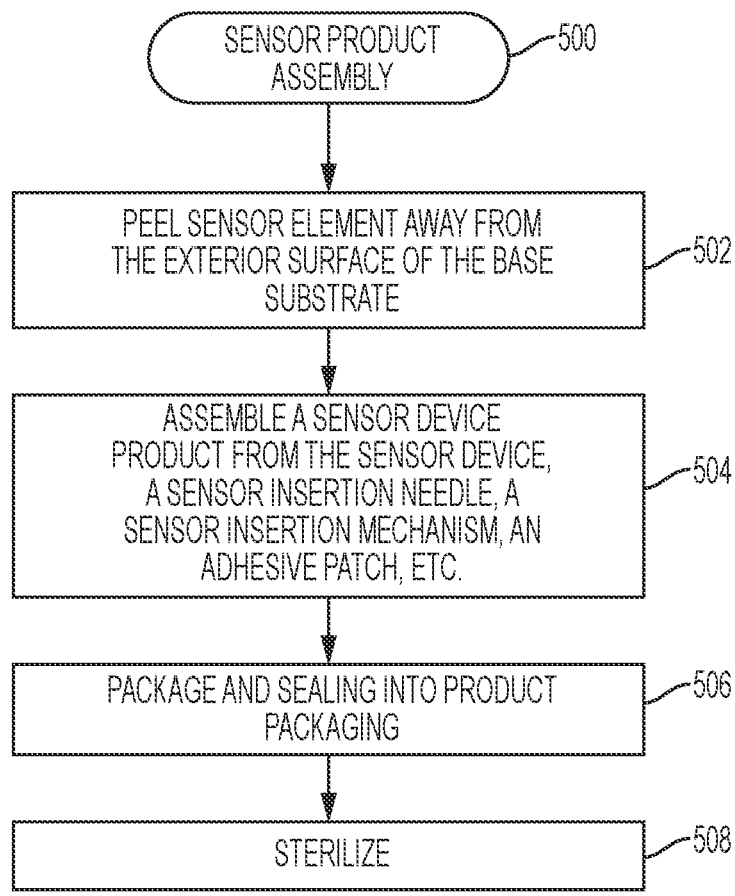
FIG. 13 is a flow chart that illustrates an exemplary embodiment of a sensor product assembly process.

FIG. 13 is a flow chart that illustrates an exemplary embodiment of a sensor product assembly process 500. The process 500 will be described with reference to FIGS. 14-16. It should be appreciated that an embodiment of the process 500 may include any number of additional or alternative tasks, the tasks shown in FIG. 13 need not be performed in the illustrated order, and the process 500 may be incorporated into a more comprehensive procedure or process having additional functionality not described in detail herein. Moreover, one or more of the tasks shown in FIG. 13 could be omitted from an embodiment of the process 500 as long as the intended overall functionality remains intact.

Figure 14:
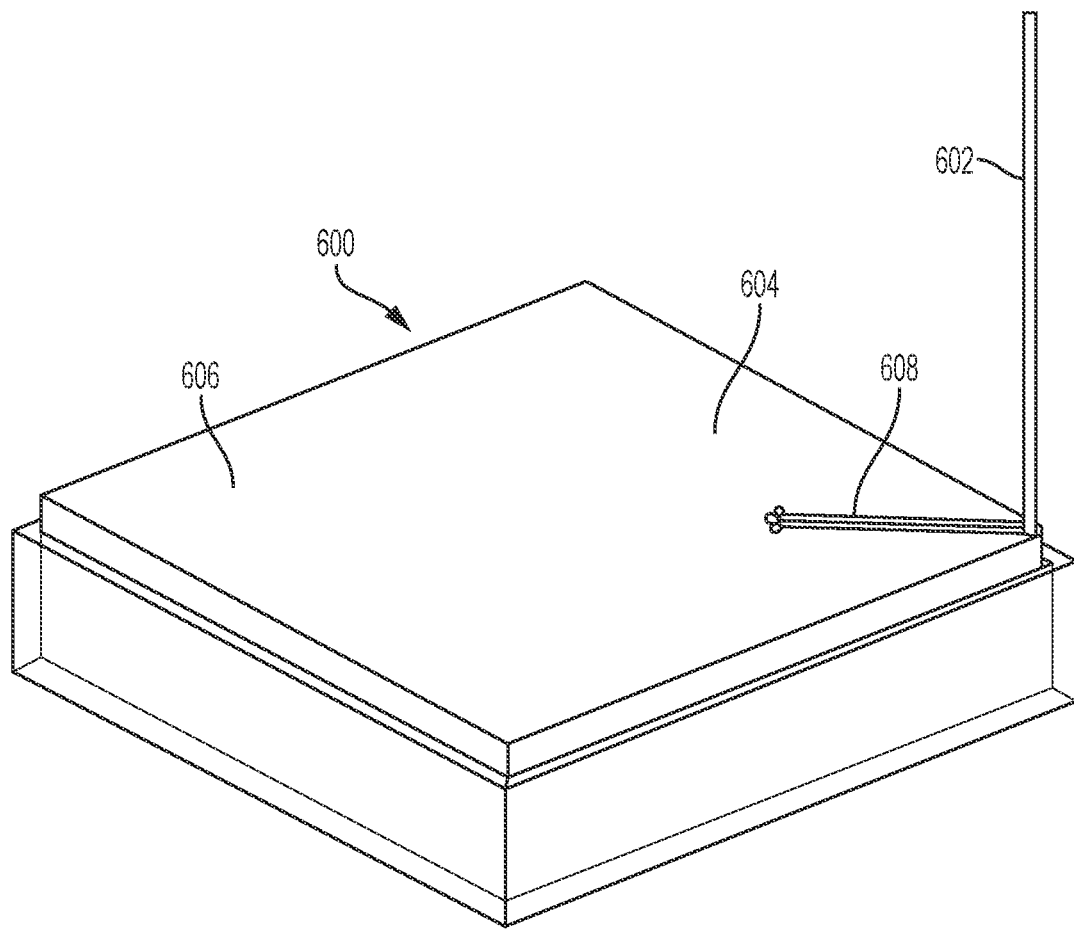
FIG. 14 is a perspective view of a singulated physiological characteristic sensor device with its sensor element deployed in an extended position.

An iteration of the sensor product assembly process 500 is performed for each of the singulated sensor device components that result from the sensor device fabrication process 300. In accordance with this particular embodiment, the assembly process 500 begins by peeling at least a portion of the physiological sensor element (e.g., the glucose sensor) away from the exterior surface of the base substrate (task 502). In this regard, FIG. 14 is a perspective view of a singulated physiological characteristic sensor device 600 with its sensor element 602 deployed in an extended position relative to the exterior surface 604 of the base substrate 606. In practice, the sensor element 602 is fabricated in a suitable manner that allows it to be easily peeled from the exterior surface 604 without compromising its structural integrity or its electro-chemical properties. To this end, the sensor element 602 can be designed and fabricated to allow the desired length to extend above the exterior surface 604, e.g., at least eight millimeters for a typical continuous glucose sensor element. Moreover, the sensor element 602 can be fabricated in a way that allows its extended length to be variable to suit the needs of different applications. In other words, the amount that is peeled away need not be the same for all instantiations of the sensor device 600. In practice, the sensor element 602 can be designed and fabricated such that a section 608 remains adhered to the exterior surface 604 to stabilize and maintain the lifted portion in position. This surface-mounted section 608 can be configured in any desired layout (e.g., a spiral, a zig-zag, or a triangle) to provide the desired amount of structural stability and integrity.

Figure 15:
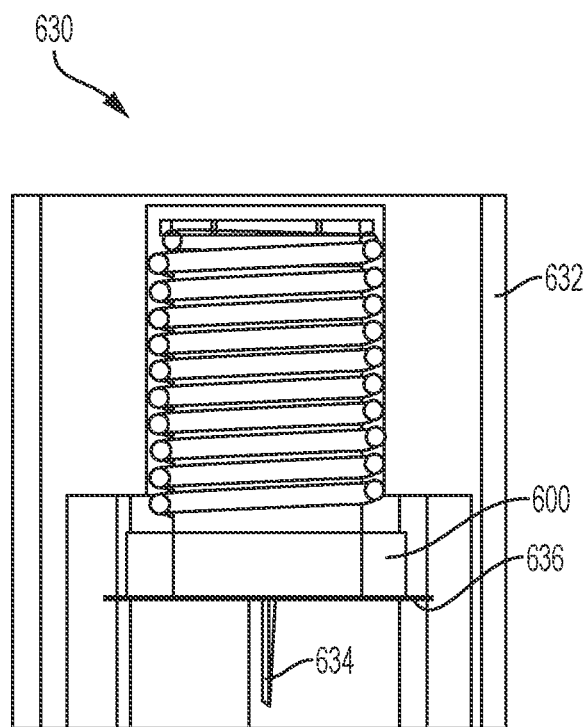
FIG. 15 is a phantom elevation view of an exemplary embodiment of a sensor device product that includes a singulated instance of a physiological characteristic sensor device, an insertion mechanism, and an insertion needle.
Figure 16:
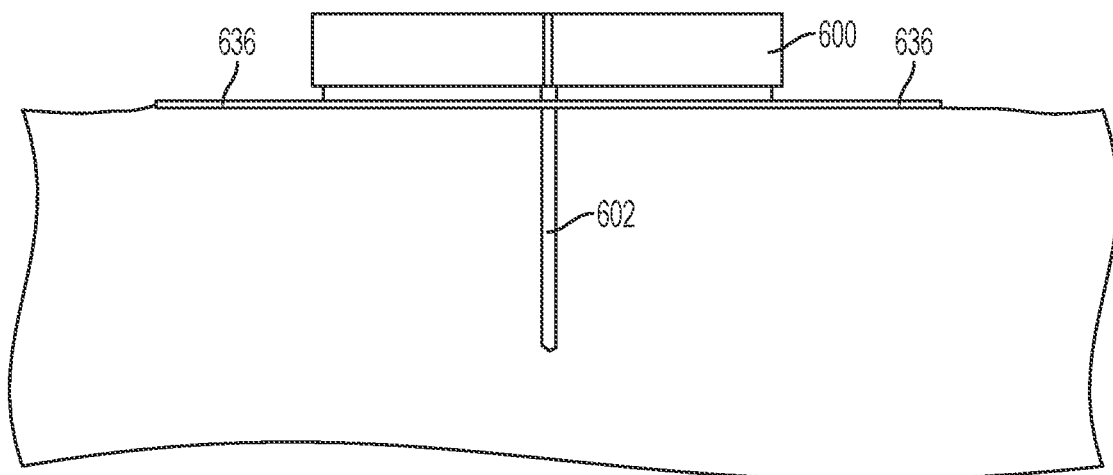
FIG. 16 is an elevation view of the physiological characteristic sensor device shown in FIG. 15, after it has been deployed for use.

Referring again to FIG. 13, the sensor product assembly process 500 continues by assembling a sensor device product from the sensor device 600 (task 504). In certain embodiments, task 504 may involve a number of assembly, handling, and manufacturing steps to create the sensor device product from the sensor device 600, a sensor insertion needle, a sensor insertion mechanism, an adhesive patch, product packaging, and the like. In this regard, FIG. 15 is a phantom elevation view of an exemplary embodiment of a sensor device product 630 that includes the sensor device 600. The illustrated embodiment includes an insertion mechanism 632, a hollow insertion needle 634, and an adhesive patch 636 (which is represented by a thin layer affixed to the bottom surface of the sensor device 600). The sensor device product 630 functions in accordance with conventional insertion devices in that the insertion mechanism 632 includes a spring-loaded plunger that holds the sensor device 600 and insertion needle 634 until activated by the user. The user holds the insertion mechanism 632 against the skin of the patient and activates the plunger to force the sensor device 600 and insertion needle 634 toward the skin of the patient. The insertion needle 634 enters the skin and the sensor device 600 is pressed against the skin to secure it with the adhesive patch 636. The insertion needle 634 is automatically retracted, leaving the free end of the sensor element deployed in the skin. Thereafter, the insertion mechanism 632 is pulled away and discarded, leaving the sensor device 600 adhered to the skin of the patient, as depicted in FIG. 16 (and in FIG. 1).

In certain embodiments, task 504 may involve any or all of the following steps (listed in no particular order): affixing the adhesive patch 636 to the bottom of the sensor device 600; installing the sensor device 600 into the housing of the insertion mechanism 632; feeding the sensor element 602 into the insertion needle 634; and loading the actuation spring of the insertion mechanism 632. The vias and conductive plugs formed in the base substrate can be designed and configured to provide mechanical support for the insertion needle 634 during final assembly. In this regard, a counterbore methodology can be employed to provide support for the insertion needle 634. It should be appreciated that insertion devices for implantable sensors are well known and, therefore, the embodiment depicted in FIG. 15 will not be described in detail here.

Referring again to FIG. 13, the sensor product assembly process 500 may continue by packaging and sealing the assembled sensor device product 630 into appropriate product packaging (task 506). For example, the assembled sensor device product 630 can be placed into a protective plastic tray or bag, sealed, and labeled if so desired. The packaged product is sterilized (task 508) before storage, shipping, etc. In accordance with the exemplary embodiment contemplated here, the packaged product is subjected to an ethylene oxide (EtO) chemical or electron beam sterilization process. Of course, any suitable and appropriate sterilization technique or methodology can be utilized during task 508. That said, the design of the sensor device product 630 and its packaging must be compatible with the desired sterilization methodology. In this regard, certain embodiments of the sensor device fabrication process 300 utilize ultraviolet (UV) based glucose oxidase and a glucose limiting membrane to allow for an ethylene oxide sterilization process. The glucose oxidase is immobilized using an appropriate UV exposure, which makes it compatible with ethylene oxide and, therefore, suitable for ethylene oxide sterilization.

Alternative Embodiments and Variations

The exemplary embodiment described above with reference to FIGS. 2 and 7-9 includes certain functional component layers stacked atop one another. In practice, a sensor device package can be fabricated according to the methodologies described herein using any number of component layers, including only one. A given component layer can include passive devices, active components, a power source, or any combination thereof. In other words, a component layer of the sensor device can include any mix or blend of elements, devices, or features. In addition, the number of component layers and the order in which they appear in the stack can differ from that depicted above. Indeed, the sensor device can include a single component layer that includes all of the required functionality, including the elements described previously for the distinct passive component, active, and power source component layers. The particular arrangement shown in FIG. 2 and described in detail above is merely one possible implementation of a sensor device manufactured in accordance with the exemplary fabrication process.

Figure 17:
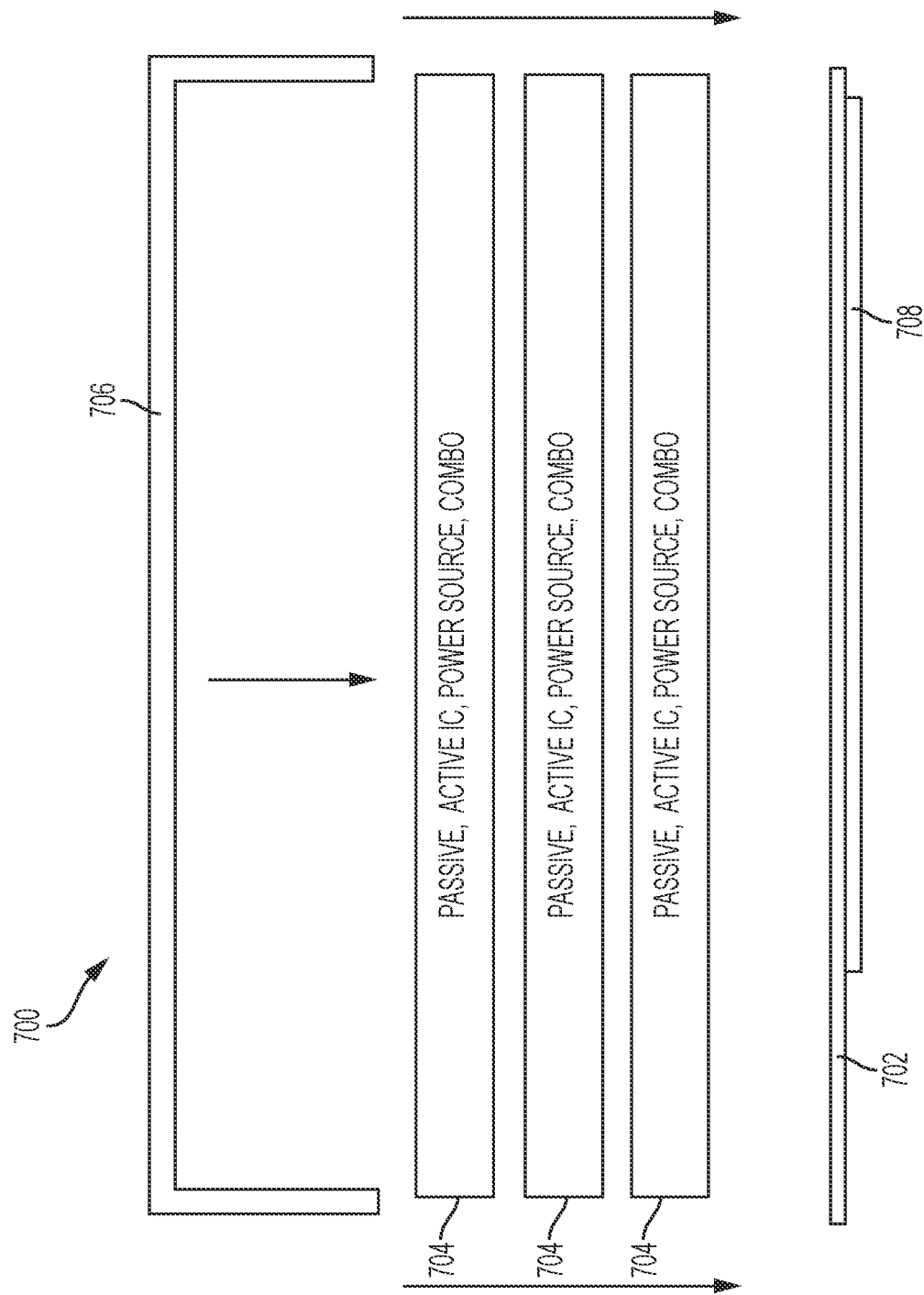
FIG. 17 is a diagram that illustrates an embodiment of a sensor device fabrication process.

FIG. 17 is a diagram that illustrates an embodiment of a sensor device fabrication process. In accordance with this embodiment, the sensor device 700 employs a base substrate 702 as a foundation. One or more component layers 704 are built upwards overlying the base substrate 702. As indicated in FIG. 17 (and as described in the preceding paragraph), each component layer 704 may be a passive component layer, an active layer, a power source layer, or any combination thereof. FIG. 17 depicts three component layers 704 for consistency with FIG. 2; in practice, any number of component layers 704 can be utilized. The sensor device 700 is capped or enclosed with an enclosure structure 706, which can be created from a second substrate with cavities formed therein. The sensor element 708 is formed on the surface of the base substrate 702. FIG. 17 depicts the sensor element 708 before it has been peeled away from the surface of the base substrate.

Figure 18:
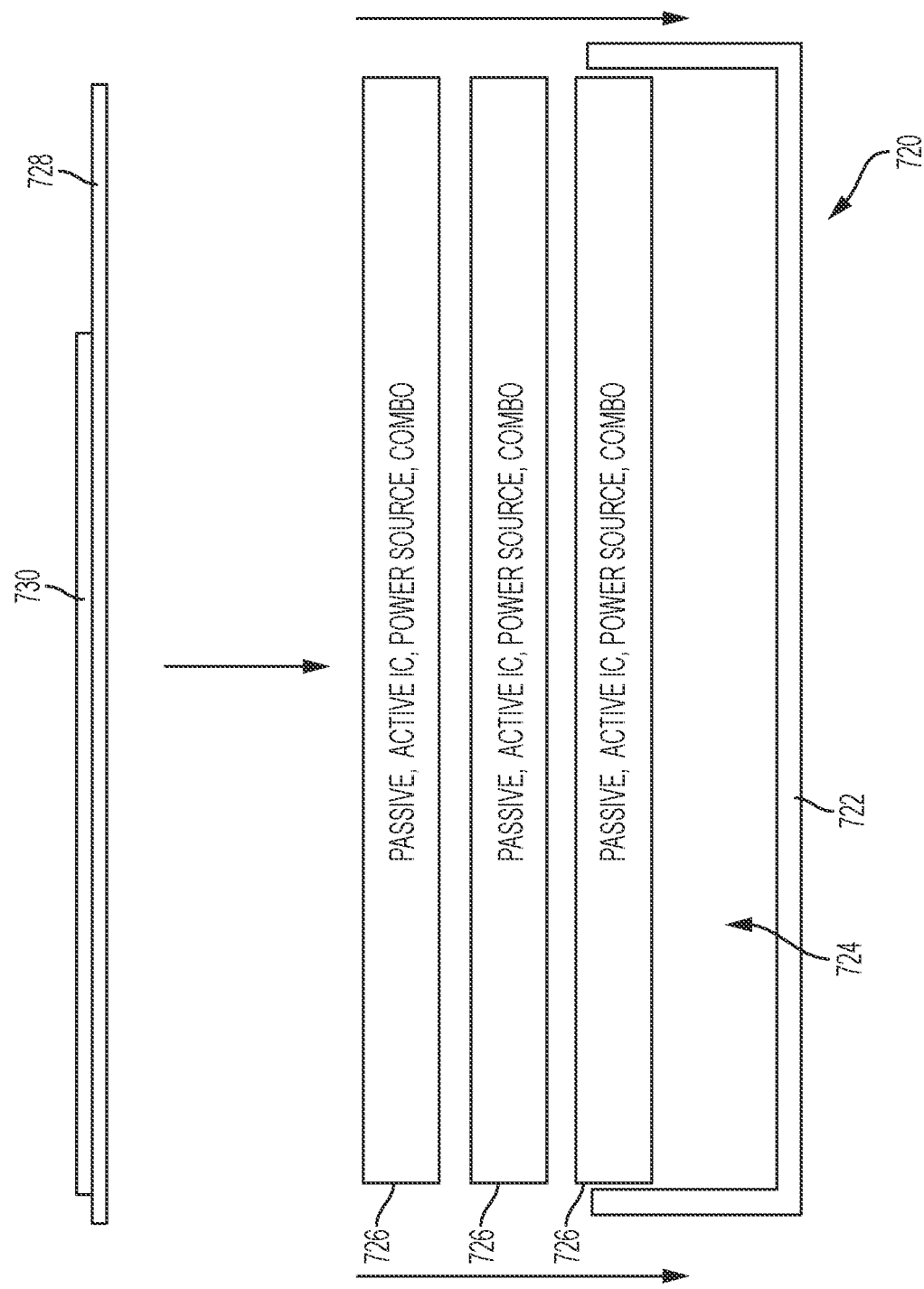
FIG. 18 is a diagram that illustrates another embodiment of a sensor device fabrication process.

FIG. 18 is a diagram that illustrates another embodiment of a sensor device fabrication process. In accordance with this embodiment, the sensor device 720 employs an enclosure structure 722 as a foundation. The enclosure structure has a component cavity 724 defined therein. For this fabrication process, one or more component layers 726 are built or introduced inside the component cavity 724. As indicated in FIG. 18 (and as described above), each component layer 726 may be a passive component layer, an active layer, a power source layer, or any combination thereof. FIG. 18 depicts three component layers 726 for consistency with FIG. 2; in practice, any number of component layers 726 can be utilized. The sensor device 720 is capped or enclosed with a substrate 728, which serves as a lid or a cap for the component cavity 724. The sensor element 730 is formed on the surface of the substrate 728. FIG. 18 depicts the sensor element 730 before it has been peeled away from the surface of the substrate 728. As explained above with reference to FIGS. 2-16, conductive plug elements formed in the substrate 728 provide electrical connections from the electrodes of the sensor element 730 to a circuit pattern and/or an interconnect arrangement of the multilayer component stack.

Figure 19:
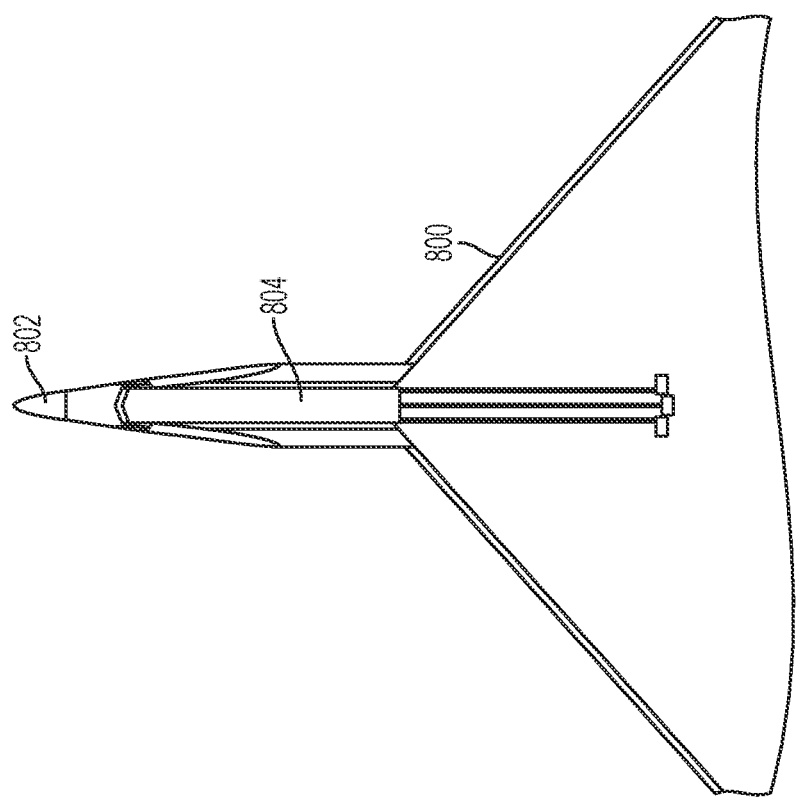
FIG. 19 is a bottom perspective view of a portion of a sensor device and an insertion needle according to an exemplary embodiment.

FIG. 19 is a bottom perspective view of a portion of a sensor device 800 and an insertion needle 802 according to an exemplary embodiment. FIG. 19 illustrates one technique for feeding the sensor element 804 into the hollow space of the insertion needle 802. In this regard, the corner of the sensor device can be utilized as a guide that allows the insertion needle 802 to "slide" up and onto the sensor element 804 during task 504 of the process 500. This technique is practical when the insertion needle 802 has an open side or longitudinal cutout that can accommodate the corner of the sensor device 800.

Figure 20:
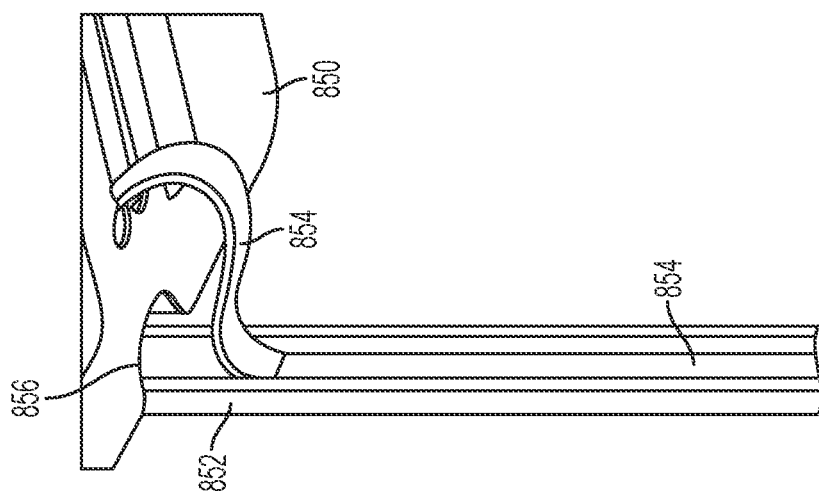
FIG. 20 is a bottom perspective view of a portion of a sensor device and an insertion needle according to another exemplary embodiment.

FIG. 20 is a bottom perspective view of a portion of a sensor device 850 and an insertion needle 852 according to another exemplary embodiment. FIG. 20 illustrates another approach for feeding the sensor element 854 into the insertion needle 852. In this embodiment, the edge of the sensor device 850 has a cutout 856 formed therein, and the cutout accommodates the insertion needle 852. This allows the insertion needle 852 to slide through the cutout 856 while the sensor element 854 is threaded into the hollow space of the insertion needle 852.

In certain embodiments, the insertion needle for the sensor element is integrated directly with the sensor device. In other embodiments, the insertion needle is integrated with the sensor device indirectly, using another component such as the insertion mechanism. For example, the insertion needle 852 depicted in FIG. 20 can be attached to a mounting hub or knob, which in turn is integrally coupled with the sensor device 850 such that the insertion needle 852 is directly integrated with the sensor device 850. In an alternative implementation, the insertion needle can be implemented as a part of the insertion mechanism. In such an implementation, the sensor element can be threaded into the insertion needle when the sensor device is assembled with the insertion mechanism (such that the insertion needle is indirectly integrated with the sensor device, via the insertion mechanism).

The sensor devices and sensor device products described here are less expensive to fabricate, package, and assemble, relative to a traditional arrangement that requires a sensor device component and a physically distinct wireless transmitter component. Moreover, the integration of sensor and transmitter functionality into a single unitary device package makes it much easier to manage, handle, and deploy (from the patient's perspective). Furthermore, the inexpensive nature of the sensor device product described here enables it to be sold as a disposable item. These and other practical benefits can be realized through the use of such sensor devices.

While at least one exemplary embodiment has been presented in the foregoing detailed description, it should be appreciated that a vast number of variations exist. It should also be appreciated that the exemplary embodiment or embodiments described herein are not intended to limit the scope, applicability, or configuration of the claimed subject matter in any way. Rather, the foregoing detailed description will provide those skilled in the art with a convenient road map for implementing the described embodiment or embodiments. It should be understood that various changes can be made in the function and arrangement of elements without departing from the scope defined by the claims, which includes known equivalents and foreseeable equivalents at the time of filing this patent application.

What is claimed is:

1. A method of fabricating a sensor device, the method comprising:
   filling a via of a substrate with a conductive material to define a conductive plug element, wherein the via extends from an exterior surface of the substrate to an interior surface of the substrate;
   electrically coupling a physiological characteristic sensor element to a first end of the conductive plug element on the exterior surface of the substrate, wherein the physiological characteristic sensor element comprises sensor electrodes, and wherein the via and the conductive plug element are configured to employ a counterbore methodology to provide mechanical support for an insertion needle for deploying the physiological characteristic sensor element in a user;
   electrically coupling a multilayer component stack to a second end of the conductive plug element on the interior surface of the substrate, wherein the multilayer component stack is configured to process and wirelessly communicate sensor data obtained by the physiological characteristic sensor element; and
   coupling the substrate to an enclosure structure defining a component cavity, and wherein the interior surface of the substrate faces the component cavity, and wherein the substrate encloses the multilayer component stack inside the component cavity.

2. The method of claim 1, further comprising coupling the insertion needle to the conductive plug, wherein the at least a portion of the physiological characteristic sensor element extends into a lumen defined by the insertion needle.

3. The method of claim 1, further comprising peeling at least a portion of the physiological sensor element away from the exterior surface of the substrate.

4. The method of claim 3, further comprising:
   inserting the portion of the physiological sensor element into a lumen defined by the insertion needle; and
   coupling at least a portion of the insertion needle to the conductive plug.

5. The method of claim 1, further comprising forming on the physiological characteristic sensor element a sensor chemistry comprising glucose oxidase.

6. The method of claim 1, wherein the multilayer component stack comprises an active layer, a passive component layer, and a power source component layer.

7. The method of claim 1, further comprising forming a conductive circuit pattern on the interior surface of the substrate.

8. The method of claim 1, further comprising physically coupling the multilayer component stack to the interior surface of the substrate.

9. The method of claim 1, further comprising forming the component cavity in the enclosure structure.

10. The method of claim 1, further comprising filling a second via and a third via of the substrate with the conductive material to define a second conductive plug element and a third conductive plug element.

11. The method of claim 1, further comprising affixing an adhesive patch to at least a portion of the exterior surface of the substrate.

12. The method of claim 1, further comprising installing the sensor device into an insertion mechanism and loading an actuation spring of the insertion mechanism.

13. A method of fabricating a plurality of sensor devices, the method comprising:
   filling a plurality of vias of a substrate with a conductive material to define a plurality of conductive plug elements, wherein the substrate defines a plurality of die locations, and wherein each respective via extends from an exterior surface of the substrate to an interior surface of the substrate;
   electrically coupling a respective physiological characteristic sensor element to a respective first end of each conductive plug element of the plurality of conductive plug elements on the exterior surface of the substrate, wherein each respective physiological characteristic sensor element comprises sensor electrodes, and wherein each via and corresponding conductive plug element are configured to employ a counterbore methodology to provide mechanical support for a respective insertion needle for deploying the respective physiological characteristic sensor element in a user;

electrically coupling a respective multilayer component stack of a plurality of multilayer component stacks to a respective second end of each conductive plug element on the interior surface of the substrate, wherein each respective multilayer component stack is configured to process and wirelessly communicate sensor data obtained by the respective physiological characteristic sensor element; and coupling the substrate to an enclosure structure defining a plurality of component cavities, wherein each respective component cavity corresponds to a respective die location of the plurality of die locations, wherein the interior surface of the substrate faces the component cavity, and wherein the substrate encloses each multilayer component stack inside a respective component cavity.

14. The method of claim 13, further comprising separating each respective sensor device of the plurality of sensor devices from adjacent sensor devices.

15. The method of claim 13, further comprising forming on each respective physiological characteristic sensor element of the plurality of physiological characteristic sensor elements a sensor chemistry comprising glucose oxidase.

16. The method of claim 13, further comprising forming a respective conductive circuit pattern of a plurality of conductive circuit patterns at each respective die location on the interior surface of the substrate.

17. The method of claim 13, further comprising physically coupling each respective multilayer component stack of the plurality of multilayer component stack at each respective die location on the interior surface of the substrate.

18. The method of claim 13, further comprising forming the plurality of component cavities in the enclosure structure.

19. The method of claim 13, wherein each respective die location of the plurality of die locations comprises at least three conductive plug elements.

20. The method of claim 13, wherein each respective multilayer component stack comprises an active layer, a passive component layer, and a power source component layer.

* * * * *